(12) United States Patent
Kliman

(10) Patent No.: US 8,521,273 B2
(45) Date of Patent: Aug. 27, 2013

(54) DRUG DELIVERY DEVICES, KITS AND METHODS THEREFOR

(76) Inventor: Gilbert H. Kliman, Portola Valley, CA (US)

(*) Notice: Subject to any disclaimer, the term of this patent is extended or adjusted under 35 U.S.C. 154(b) by 502 days.

(21) Appl. No.: 12/362,460

(22) Filed: Jan. 29, 2009

(65) Prior Publication Data

US 2009/0196903 A1    Aug. 6, 2009

Related U.S. Application Data

(60) Provisional application No. 61/024,462, filed on Jan. 29, 2008.

(51) Int. Cl.
*A61N 1/30* (2006.01)
(52) U.S. Cl.
USPC ............ 604/20; 604/21; 604/521; 604/890.1; 604/891.1
(58) Field of Classification Search
USPC .................. 604/20, 21, 521, 890.1, 891.1
See application file for complete search history.

(56) References Cited

U.S. PATENT DOCUMENTS

| | | | |
|---|---|---|---|
| 4,702,228 A | 10/1987 | Russell, Jr. et al. | |
| 4,784,116 A | 11/1988 | Russell, Jr. et al. | |
| 4,891,043 A * | 1/1990 | Zeimer et al. | 604/20 |
| 5,098,443 A | 3/1992 | Parel et al. | |
| 5,551,427 A | 9/1996 | Altman | |
| 5,773,019 A | 6/1998 | Ashton et al. | |
| 5,797,898 A | 8/1998 | Santini, Jr. et al. | |
| 6,080,099 A | 6/2000 | Slater et al. | |
| 6,123,861 A | 9/2000 | Santini, Jr. et al. | |
| 6,196,993 B1 | 3/2001 | Cohan et al. | |
| 6,403,916 B1 | 6/2002 | Spooner et al. | |
| 6,464,687 B1 | 10/2002 | Ishikawa et al. | |
| 6,474,535 B1 | 11/2002 | Shanks et al. | |
| 6,491,666 B1 | 12/2002 | Santini, Jr. et al. | |
| 6,527,762 B1 | 3/2003 | Santini, Jr. et al. | |
| 6,537,192 B1 | 3/2003 | Elliott et al. | |
| 6,548,078 B2 * | 4/2003 | Guo et al. | 424/423 |
| 6,669,622 B2 | 12/2003 | Reed et al. | |

(Continued)

FOREIGN PATENT DOCUMENTS

| | | |
|---|---|---|
| EP | 0914092 B1 | 4/2002 |
| EP | 1210064 B1 | 3/2005 |

(Continued)

OTHER PUBLICATIONS

Huttman, G. et al. (Jun. 8, 2005). "New concepts in laser medicine: Towards a laser surgery with cellular precision," *Medical Laser Application* 20 (2):135-139.

(Continued)

*Primary Examiner* — Bhisma Mehta
(74) *Attorney, Agent, or Firm* — Sutherland Asbill & Brennan LLP

(57) ABSTRACT

Implantable drug delivery devices, and kits and methods incorporating them are described. The devices may, for example, be configured for implantation into an ocular region of a subject. The drug delivery devices may comprise multiple, selectively-triggerable drug reservoirs for administration of sequential or concomitant drug regimens. Some variations of devices may comprise one or more reservoirs that may be triggered by an optical stimulus, e.g., light having a wavelength within a certain wavelength range. The devices, methods, and kits may be useful in the treatment chronic ocular conditions, such as age-related macular degeneration.

55 Claims, 15 Drawing Sheets

(56) References Cited

U.S. PATENT DOCUMENTS

| | | |
|---|---|---|
| 6,716,156 B2 | 4/2004 | Menuhr et al. |
| 6,719,750 B2 | 4/2004 | Varner et al. |
| 6,730,072 B2 | 5/2004 | Shawgo et al. |
| 6,808,522 B2 | 10/2004 | Richards et al. |
| 6,846,283 B2 | 1/2005 | Green et al. |
| 6,849,463 B2 | 2/2005 | Santini, Jr. et al. |
| 6,875,208 B2 | 4/2005 | Santini, Jr. et al. |
| 6,976,982 B2 | 12/2005 | Santini, Jr. et al. |
| 6,989,007 B2 | 1/2006 | Shadduck |
| 7,070,590 B1 | 7/2006 | Santini, Jr. et al. |
| 7,070,592 B2 | 7/2006 | Santini, Jr. et al. |
| 7,117,870 B2 | 10/2006 | Prescott |
| 7,200,432 B2 | 4/2007 | Lerner et al. |
| 7,207,965 B2 | 4/2007 | Simon et al. |
| 7,226,442 B2 | 6/2007 | Sheppard, Jr. et al. |
| 7,282,046 B2 | 10/2007 | Simon et al. |
| 7,354,597 B2 | 4/2008 | Johnson et al. |
| 7,410,616 B2 | 8/2008 | Santini, Jr. et al. |
| 7,445,766 B2 | 11/2008 | Santini, Jr. et al. |
| 7,473,248 B2 | 1/2009 | Santini, Jr. et al. |
| 7,488,316 B2 | 2/2009 | Prescott et al. |
| 7,497,846 B2 | 3/2009 | Uhland et al. |
| 7,534,241 B2 | 5/2009 | Coppeta et al. |
| 7,563,255 B2 | 7/2009 | Adamis et al. |
| 7,874,974 B2 | 1/2011 | Terwilliger et al. |
| 2003/0176854 A1 | 9/2003 | Rodstrom |
| 2004/0133155 A1 | 7/2004 | Varner et al. |
| 2004/0247671 A1 | 12/2004 | Prescott et al. |
| 2004/0254521 A1 | 12/2004 | Simon |
| 2005/0136094 A1 | 6/2005 | Watson et al. |
| 2005/0143715 A1 | 6/2005 | Cima et al. |
| 2005/0149000 A1 | 7/2005 | Santini et al. |
| 2005/0196424 A1* | 9/2005 | Chappa .................... 424/423 |
| 2005/0208103 A1 | 9/2005 | Adamis et al. |
| 2006/0013835 A1 | 1/2006 | Anderson et al. |
| 2006/0018963 A1 | 1/2006 | Cucala Escoi et al. |
| 2006/0069340 A1 | 3/2006 | Simon |
| 2006/0129129 A1 | 6/2006 | Smith |
| 2006/0216329 A1 | 9/2006 | Peyman |
| 2006/0253151 A1 | 11/2006 | Nun |
| 2007/0026048 A1 | 2/2007 | Greenberg |
| 2007/0135753 A1* | 6/2007 | Barres et al. .................... 604/19 |
| 2007/0275035 A1* | 11/2007 | Herman et al. ............... 424/426 |
| 2008/0047926 A1 | 2/2008 | Santini et al. |
| 2008/0051766 A1 | 2/2008 | Santini et al. |
| 2008/0071252 A1 | 3/2008 | Santini et al. |
| 2008/0152654 A1* | 6/2008 | Reich ........................ 424/145.1 |
| 2008/0177153 A1 | 7/2008 | Bachman et al. |
| 2008/0221555 A1 | 9/2008 | Sheppard et al. |
| 2008/0221557 A1 | 9/2008 | Santini et al. |

FOREIGN PATENT DOCUMENTS

| | | |
|---|---|---|
| EP | 1235560 B1 | 4/2006 |
| EP | 1313415 B1 | 8/2008 |
| EP | 1992317 A2 | 11/2008 |
| WO | WO-02/55058 A2 | 7/2002 |
| WO | WO-2004/098565 A2 | 11/2004 |
| WO | WO-2005/120393 A2 | 12/2005 |
| WO | WO-2006/014484 A2 | 2/2006 |
| WO | WO-2006/077528 A2 | 7/2006 |
| WO | WO-2006/110487 A1 | 10/2006 |
| WO | WO-2007/083293 A1 | 7/2007 |
| WO | WO-2007/084765 A2 | 7/2007 |

OTHER PUBLICATIONS

International Search Report mailed Aug. 10, 2009, for PCT Application No. PCT/UC2009/032500 filed Jan. 29, 2009, 8 pages.

Lo, et al. (2008). "A refillable microfabricated drug delivery device for treatment of ocular diseases," *Lab Chip* 8:1027-30.

Santini et al. (1999). "A controlled-release microchip," *Nature* 397:335-338.

* cited by examiner

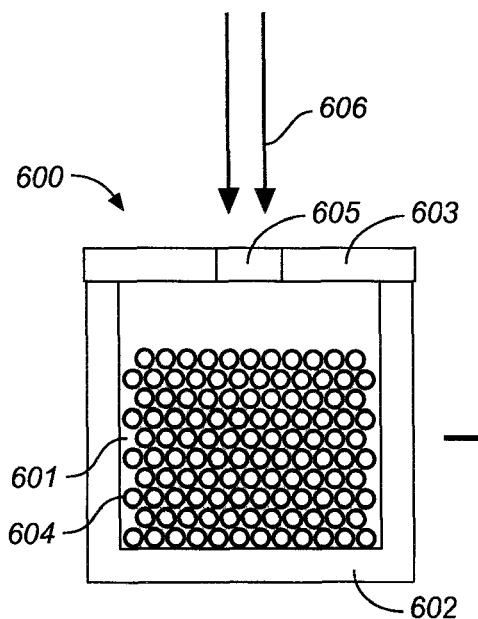 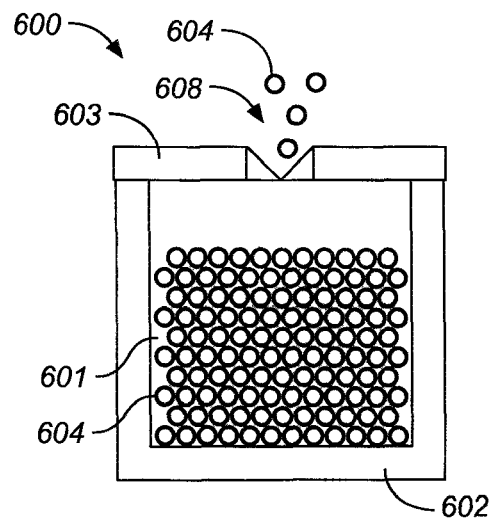
FIG. 6A  FIG. 6B
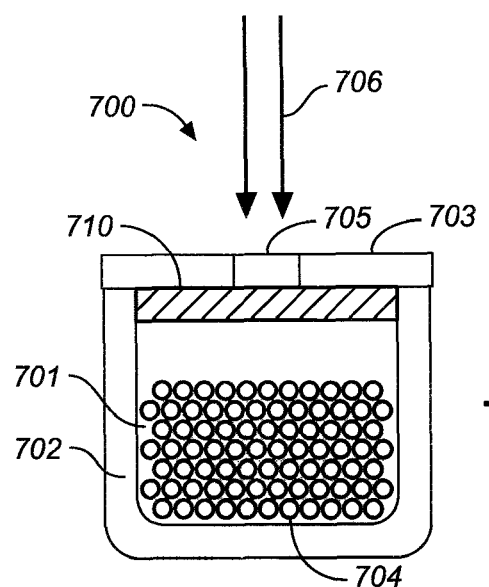 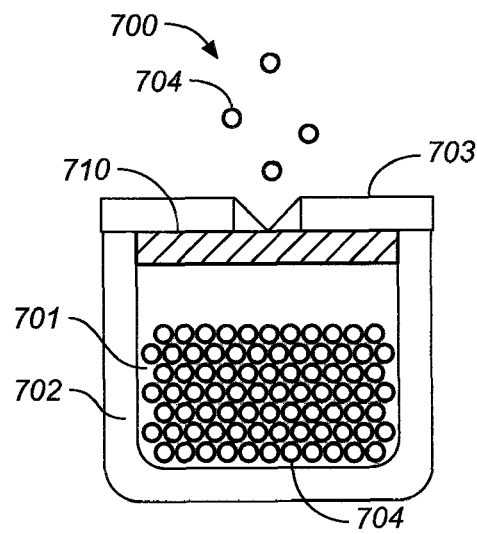
FIG. 7A  FIG. 7B

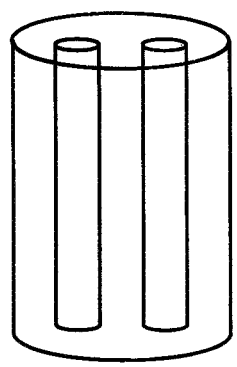 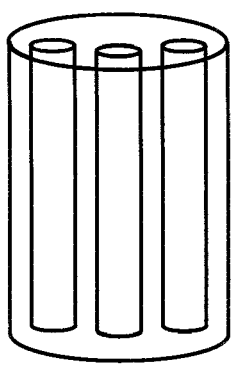 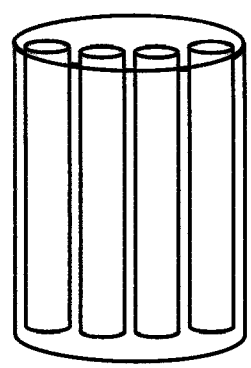
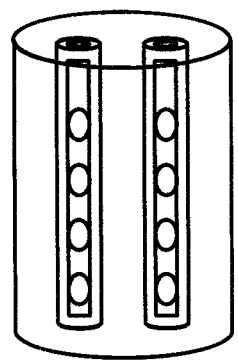 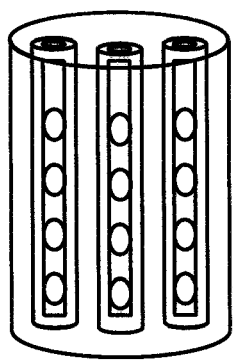 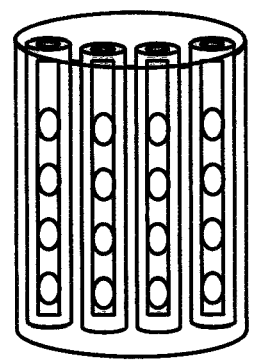
*FIG. 13A*  *FIG. 13B*  *FIG. 13C*

DRUG DELIVERY DEVICES, KITS AND METHODS THEREFOR

CROSS-REFERENCE TO RELATED APPLICATIONS

This application claims the benefit of U.S. Provisional Application Ser. No. 61/024,462, filed Jan. 29, 2008, which is hereby incorporated by reference in its entirety.

FIELD

This application relates to implantable drug delivery devices, and in particular, to drug delivery devices for implantation in an eye. This application also relates to methods of using implantable drug delivery devices, and kits that include them.

BACKGROUND

In many instances, a drug's efficacy may be affected by the manner in which it is delivered to the body. Drugs may be administered using a variety of controlled-release or sustained-release technologies. For example, drug pumps, patches, and controlled-release tablet formulations may be used for drug administration.

Many chronic eye conditions require sustained or repeated delivery of drugs to the eye. However, systemic delivery of drugs to the eye may be limited by transfer through the blood-ocular barrier, thus requiring very high systemic doses that may lead to toxicity. Commonly, liquid eye drops may be used to administer drugs to the eye. However, only low molecular weight drugs effectively diffuse through ocular tissue. Thus, not all drugs can be formulated in liquid drop form. Other times, drugs may be administered to the posterior of the eye by intravitreal injection. However, repeated intraocular injections may lead to increased risk of infection or damage to the eye. Ocular implants have also been developed, but their use has been limited due to the small size and shape of the eye, and the technical complexity of controlled long term drug delivery.

Given the benefits of targeted drug delivery and the need for complex and/or extended drug therapies to treat some conditions, improved drug delivery devices are desirable. For example, implantable drug delivery devices with improved drug-release schemes to enable user-controlled or physician-controlled delivery of a single drug, or a combination of multiple drugs or drug doses, would be desirable. In particular, improved implantable drug delivery devices for use in the eye are needed.

SUMMARY

Described here are drug delivery devices, kits comprising such devices, and methods for using the devices. The devices may be configured for use in a variety of locations within the body, and for a variety of applications. For example, the drug delivery devices may be used for a variety of immediate or extended drug regimens, including the controlled delivery of multiple drugs and/or multiple doses of drugs.

In general, the drug delivery devices may be configured for implantation into a subject, e.g., into an ocular region. Variations of implantable drug devices may comprise one or more drug reservoirs configured to be loaded with a drug, and to subsequently release the drug to the body. Some devices may comprise multiple reservoirs for delivering multiple drugs and/or multiple doses of drugs. Of course, a single reservoir may contain more than one drug, e.g., a combination of drugs. In some variations, the drug delivery devices are configured to have a therapeutic portion and a diagnostic portion. Here the reservoirs may be provided on the therapeutic portion of the device, and triggered to release a drug in response to a signal that is directly or indirectly transmitted by the diagnostic portion of the device.

The reservoirs within a drug delivery device may be triggered to release one or more drugs, e.g., with a stimulus. In some instances, the device includes a target region that is configured to enable release of a drug upon being stimulated. In other instances, the device includes one or more sensors capable of indicating when a reservoir should be triggered to enable release of a drug. In yet further instances, a combination of such target regions and sensors are included on the device that work together or individually to release one or more drugs. In certain variations, the drug is not contained within a reservoir, but is rather provided in a coating on all or a portion of the device. Here a trigger, e.g., a stimulus, may be used to release one or more drugs contained within the coating, in the same fashion as described for the reservoirs.

It should be understood that any type of stimulus may be used to trigger a reservoir to release a drug. Non-limiting examples of suitable stimuli include, optical, mechanical, chemical, electrical, magnetic, acoustic (e.g., ultrasound), radiofrequency, other radiative (e.g., ionizing radiation), and thermal stimuli, and combinations thereof. Some devices may comprise a first subset of reservoirs that may be selectively triggered by a first stimulus. Some of those devices, in turn, may comprise a second subset of reservoirs that may be selectively triggered by a second stimulus. Although only first and second stimuli and reservoir subsets are mentioned here, any number of stimuli and reservoir subsets may be used.

After triggering a reservoir to release a drug, the drug may be released in any suitable manner and according to any suitable release profile. For example, and as further described below, a stimulus may trigger drug release by inducing one or multiple modifications to the reservoirs. In some variations, e.g., when capped reservoirs are employed, the triggering may comprise stimulating the reservoir to open one or more orifices or pores in the caps upon reservoir stimulation through which a drug can directly exit the reservoir. In other variations, the triggering may comprise stimulating the reservoir to open orifices or pores, which may then expose a portion of a rate release membrane through which a drug can be delivered. In yet further variations, the triggering may include applying a stimulus to the reservoir that may then modify the material of the reservoir, e.g., the reservoir cap, or other portion of the device, to effect a change in its permeability, e.g., by inducing molecular changes in the material.

Upon triggering a reservoir to release a drug, drug release may occur in any suitable manner. For example, the drug may be released actively by an active mechanism (e.g., by a pump, injector, etc.) or passively (e.g., by diffusion or dissolution). The drug may also be released according to any type of release profile. For example, the devices may be configured to release a drug according to a continuous release, pulsed release, burst release (i.e., large initial release), bolus release (i.e., entire reservoir emptied immediately following being triggered by a stimulus), or zero-order release profiles. Other modified drug release profiles are also contemplated. For example, the reservoirs may be configured for controlled release (i.e., controlled rate of release over an extended time period) or sustained release (i.e., slow release over time, but not necessarily at a controlled rate of release) of drugs.

When multiple reservoirs are employed, the device may be configured so that all or some of the reservoirs are triggered at the same time or individually. Likewise, upon being triggered, the reservoirs may release a drug according to the same release profile or a combination of different release profiles. Although reservoirs will generally be triggered to release one or more drugs in response to a stimulus, in some instances the reservoirs may be configured to release a drug without being triggered. The drug in this instance may be released from a reservoir or from a coating on all or a portion of the device.

The devices and their associated drug reservoirs may have a variety of configurations. Devices may comprise an array of reservoirs, e.g., a linear array, a two-dimensional array, or a three-dimensional array. In some variations, multiple reservoirs may be coupled together. In other variations, multiple reservoirs may be separate from each other, e.g., one or more reservoirs in a device may separate from other reservoirs after implantation. Some devices may comprise a tether or other feature to allow repositioning, retrieval and/or securing the device while it is implanted in the body. Variations of devices may comprise an attachment configured to allow the device to be secured to the subject's anatomy. Such attachments may allow permanent or temporary securing of the device to the anatomy, e.g., attachments may be biodegradable to dissolve over time.

Target regions, if present in a device, may have any suitable composition, configuration and geometry that allow a selective response to a stimulus, e.g., an optical stimulus. For example, a target region may be a discrete part of the reservoir to be triggered, e.g., a discrete region having a well-defined geometry or other feature on a surface of the reservoir. A target region may also be a larger part of the reservoir, e.g., a surface, wall, cap, or other portion of the reservoir. In some variations, a target region may comprise a band that extends circumferentially around at least part of a circumference of the device. This latter geometry may allow improved access to the target region from an externally directed triggering stimulus (e.g., a laser) even if the device rotates in vivo. A target region may be visually differentiated from one or more non-target portions of the device.

The drug delivery devices may be configured to deliver any suitable agent (i.e., drug) or combination of agents to a subject. In devices comprising multiple reservoirs, two or more of the reservoirs may comprise the same agent, e.g., to deliver sequential doses of that agent. Reservoirs may be loaded with multiple agents that are selected to be at least part of a combination drug therapy, e.g., a concomitant drug therapy that comprises the simultaneous delivery of multiple agents and/or a sequential drug therapy that comprises the sequential delivery of multiple agents. At least one of the agents to be delivered by the devices may be selected from the group consisting of anti-inflammatories (e.g., steroidal and non-steroidal), anti-infectives (e.g., antibiotics, antifungals, antivirals, and antiseptics), anti-allergens, neuroprotection agents, anti-glaucoma agents, antioxidants, agents for cataract prevention and/or treatment, adrenergic agonists and antagonists, cholinergic agonists and antagonists, antihistamines, anti-platelet agents, anti-coagulants, anti-thrombic agents, anti-scarring agents, anti-proliferatives, anti-tumor agents, complement inhibitors, decongestants, vitamins, growth factors, anti-growth factor agents, gene therapy vectors, chemotherapy agents, protein kinase inhibitors, small interfering RNAs, limus family compounds, and combinations thereof.

Some variations of drug delivery devices may comprise a delivery configuration and an implanted configuration. For example, delivery configurations may be elongated, folded and/or compressed, whereas implanted configurations may comprise at least one bend or turn, be at least partially unfolded, and/or expanded. Devices may have any suitable dimensions. For example, devices in their delivery configuration may be configured for implantation in the subject through a 20 gauge or smaller cannula.

As stated above, some variations of devices may comprise one or more reservoirs that may be selectively triggered with an optical stimulus to initiate drug delivery. These drug delivery devices may comprise a first reservoir configured to be loaded with a first agent. The first reservoir may be configured to release the first agent in response to a first optical stimulus. Devices also may comprise a first target region that is configured to selectively respond to the first optical stimulus. The first optical stimulus may be any optical stimulus, but in some variations, the first optical stimulus may comprise irradiation with light having a wavelength over a first wavelength range, and the first target region may selectively absorb light within the first wavelength range.

Variations of drug delivery devices may be tuned to respond to a variety of different optical stimuli, e.g., optical stimuli having a variety of different wavelengths. For example, a target region in some devices may comprise at least one chromophore, where the at least one chromophore has been selected to absorb light over the desired wavelength range. In some variations, the first wavelength range may overlap with emission from a solid state, gas, or diode laser. Lasers may be continuous wave or pulsed. Non-limiting examples include argon ion lasers, Nd:YAG lasers, e.g., frequency doubled-Nd:YAG lasers, diode lasers (e.g., diode lasers emitting red or green light), Nd:YLF lasers, krypton ion lasers, helium-neon lasers, and pumped dye lasers. Argon ion and Nd:YAG lasers may be particularly beneficial.

As stated above, some variations of drug delivery devices comprise multiple reservoirs configured to be loaded with multiple agents. For example, a second agent within one reservoir of a drug delivery device may be the same or different from a first agent within the same reservoir or another reservoir in that device. The devices may be configured so that the first, second, and any other agents may be released in any order and/or at any rate. In device variations having reservoirs responsive to two or more stimuli, any combination of stimuli may be used. For example, if the first stimulus comprises an optical stimulus, the second stimulus may for example comprise a second optical stimulus, a thermal stimulus, a radiofrequency stimulus, an electrical stimulus, a mechanical stimulus, a magnetic stimulus, an ultrasound stimulus, a chemical stimulus, or any combination thereof.

Thus, some variations of drug delivery devices comprise a first reservoir configured to release a first agent loaded therein in response to a first optical stimulus, and a second reservoir configured to release a second agent loaded therein in response to a second optical stimulus. In these variations, the first optical stimulus may be the same or different from the second optical stimulus. Further, in some of these variations, the first reservoir may comprise a first target region configured to absorb light from first optical stimulus to initiate release of the first agent, and/or the second reservoir may comprise a second target region configured to absorb light from the second optical stimulus to initiate release of the second agent. In these variations, the first and/or second target regions may be configured to selectively absorb light over a first and second wavelength range, respectively. For example, the first and/or second target regions may each comprise a chromophore that selectively absorbs light over their respective wavelength ranges.

For devices comprising two or more reservoirs that are selectively triggerable by different optical stimuli to release two or more agents to the body, the optical stimuli may differ in any respect. For example, a first optical stimulus may comprise irradiation of the drug delivery device with a first wavelength, and a second optical stimulus may comprise irradiation of the drug delivery device with a second wavelength. In certain variations, the first optical stimulus may comprise irradiation with a first power density, and the second optical stimulus may comprise irradiation of the device with a second power density. In some cases, the spot size, shape, and/or geometry of an incident beam may be used to differentiate between stimuli.

An optical stimulus may trigger release of an agent from a drug delivery device in any suitable manner. For example, in some devices, an optical stimulus may initiate formation of an orifice in a reservoir, e.g., in a reservoir cap, leading to drug release. Alternatively, or in addition, a reservoir may be configured to change shape in response to an optical stimulus. The change in reservoir shape may lead to release of a drug. Depending on the desired drug regimen, reservoirs may be configured to release an agent as a bolus dose, or for sustained release of the agent, e.g., through dissolution of a matrix or casing comprising the agent and/or diffusion of the agent through a barrier.

Some drug delivery devices may comprise at least one reservoir configured to be loaded with an agent while the device is implanted in the subject. One or more reservoirs of a device may be configured for initial loading after implantation, whereas other reservoirs may be configured for reloading. For example, at least one reservoir may be configured for reloading with a reload agent, which may be the same or different than a previous agent contained in that reservoir.

Of course, some drug delivery devices may comprise three or more reservoirs, each configured to be loaded with an agent, and to release that agent upon being triggered by the same stimulus or different stimuli. In these variations, the three or more reservoirs may each contain the same or different agents. For example, any combination of optical, thermal, electrical, mechanical, ultrasound, magnetic, radiofrequency, other radiative (e.g., ionizing radiation), and chemical stimuli may be used. In some variations, three or more reservoirs may each be configured to selectively respond to an optical stimulus. In these variations, the reservoirs may be configured to respond to the same or different optical stimuli (e.g., different wavelengths and/or different power densities). Drug release from the three or more reservoirs may also occur in any manner, as previously described.

The drug delivery devices described here may have a number of uses, e.g., for implantation at a variety of body locations for targeted drug delivery, and/or for treatment of a variety of conditions. For drug delivery devices designed to be used in the eye, the devices may be configured for implantation into the vitreous cavity, the retina, the sclera, the cornea, the conjunctiva, and/or any space or potential space within the orbit or eye itself. In some cases, the devices may be particularly useful for treating chronic conditions. For example, some devices may be configured to treat age-related macular degeneration or diabetes-related conditions such as diabetic retinopathy. In addition, devices may be configured to treat any ocular disease or condition or combination of diseases or conditions occurring within or around the orbit, such as glaucoma, cataracts, retinal and choroidal disease, dry eye syndrome, optical neuropathy, orbital disease, uveitis, corneal conditions, and other diseases and conditions.

Still other variations of drug delivery devices are provided here. These drug delivery devices each comprise two or more drug reservoirs, each drug reservoir configured to be loaded with an agent. Thus, in these variations, devices comprise at least a first reservoir configured to be loaded with a first agent, and a second reservoir configured to be loaded with a second agent. The first and second reservoirs may each comprise first and second target regions, respectively, where the first and second target regions are configured to be visually differentiated. For example, the target regions may be color-coded, shape-coded, and/or patterned for ready visual differentiation.

In yet further variations, an implant is provided that is configured to receive one or more drug delivery devices within one or more housings of implants. The implants may be configured for repeat access to the drug delivery devices through a sealable opening or port. This is so that a drug can be loaded or reloaded into the reservoirs, or one or more drug delivery devices exchanged for another drug delivery device in vivo.

Kits are also described here. Some variations of kits may comprise an implantable drug delivery device and one or more drugs, e.g., a suite of drugs, for delivery by the drug delivery device. For example, some of these kits may comprise one or more replacement reservoirs containing one or more drugs that may be selected for loading into a drug delivery device. Certain variations of kits may comprise more than one implantable drug delivery device. Still other variations of kits may comprise at least one implantable drug delivery device and an implantation device configured to implant the drug delivery device into the anatomy of a subject. In some kits, the implantation device may comprise a 20 gauge or smaller cannula. Kits may optionally comprise a stimulus source to trigger at least one reservoir in the drug delivery device to release an agent contained therein. Non-limiting examples of stimulus sources that may be provided as part of the kits include optical, mechanical, chemical, radiofrequency, other radiative (e.g., ionizing radiation), ultrasound, magnetic, thermal and electrical sources. Variations of kits may comprise more than one drug delivery device, more than one implantation device, more than one drug, and/or more than one stimulus source. Any suitable drug delivery device or combination of drug delivery devices may be used in the kits. For example, any drug delivery device or combination of drug delivery devices described above may be used in the kits. Kits may optionally include instructions for use.

Variations of kits comprising a drug delivery device that include an optically-triggerable reservoir may comprise an optical source capable of supplying the appropriate wavelength, energy density and/or power density to trigger that reservoir to release an agent. Non-limiting examples of optical sources that may be included in some kits are light-emitting diodes, lamps, diode lasers, solid state lasers, and gas lasers. Optical sources may be continuous wave or pulsed light. For example, an optical source may be selected from the group consisting of argon ion lasers, Nd:YAG lasers, e.g., frequency-doubled Nd:YAG lasers, light-emitting diodes, lamps, diode lasers (e.g., diode lasers emitting red or green light), Nd:YLF lasers, krypton ion lasers, helium neon lasers, and dye lasers. Some kits may comprise at least one focusing apparatus and/or filtering apparatus (e.g., a spatial filtering apparatus) to adjust an energy density and/or a power density of light incident on a target region. For example, the focusing and/or filtering apparatus may be a lens that can be placed between the optical source and drug delivery device or placed on the eye itself. In some variations, the lens may be used to focus or direct the light onto the target region. In other variations, the lens is placed on the eye so that the appropriate wavelength of light is filtered through to the target region. The use of lenses that include both focusing and filtering capabilities are also contemplated.

Methods of use are also provided here. Variations of these methods may utilize drug delivery devices together with various triggers for controlled release of one or more agents to a desired anatomical region of the subject. Some methods may be particularly well-suited for treating chronic and/or progressive ocular conditions, such as age-related macular degeneration. Other ocular conditions that may be treated using the methods described here include retinal and choroidal disease, cataracts, glaucoma, dry eye syndrome, corneal conditions, optic neuropathy, orbital disease and uveitis. Variations of the methods may be used to treat conditions not limited to the eye, e.g., cancer and diabetes. For example, the methods may be used to deliver an anti-tumor agent through the eye to reach a tumor site elsewhere within the body. The devices described here may also be used with other treatment modalities. For example, the devices may be used prior to, concurrently with, or after implementation of the other treatment modality. More specifically, the devices may be used as an adjunct to systemic or local therapies, or before or after an ocular procedure. Other treatment modalities include, but are not limited to, intraocular drug therapy, photodynamic therapy (PDT), and radiation therapy.

In general, the methods comprise implanting a drug delivery device into the anatomy of a subject, where the implantable drug delivery device comprises one or more selectively addressable drug reservoirs. In some variations of the methods, the implantable drug delivery devices used each comprise a first reservoir configured to be loaded with a first agent. In one variation, triggering of the first reservoir by a first stimulus takes place. Once triggered, the first reservoir may release the first agent actively or passively. The first agent may then be released according to any suitable release profile. Triggering of the device to release the first agent may be enabled by a first target region on the device that is configured to selectively respond to a first stimulus, e.g., a first optical stimulus. These variations of methods may comprise irradiating the first target region with light having a wavelength within a first wavelength range as a first optical stimulus to trigger release of the first agent to the subject. Of course, in some of these methods, the drug delivery device to be implanted may comprise more than one drug reservoir, e.g., a second reservoir (or subsequent reservoir) preloaded with the same agent or with a second (or subsequent) agent. The second reservoir may also be configured to release a second agent upon being triggered. Any suitable second stimulus may be used. For example, the second stimulus may be selected from the group consisting of optical, thermal, electrical, mechanical, ultrasound, magnetic, chemical, radiofrequency, and other radiative (e.g., ionizing radiation) stimuli, and combinations thereof. Of course, the methods may include any number and combination of stimuli to trigger agent release, and the release of multiple agents, e.g., first and second agents, and subsequent agents, in any order, simultaneously or spaced apart with any suitable time interval, and/or at any relative rate.

Some variations of the methods may comprise irradiating a first target region of a drug delivery device with a first optical stimulus, and irradiating a second target region of a drug delivery device with a second optical stimulus. For example, in some variations of the methods, the first optical stimulus has a different wavelength than the second optical stimulus. Alternatively, or in addition, the first optical stimulus may have a different energy and/or power density than the second optical stimulus. The first and second optical stimuli may be applied in any order, simultaneous, or spaced apart with any suitable time interval.

Any suitable drug regimen may be administered using the methods described here. For example, the methods may comprise releasing multiple agents to provide a combination drug therapy, e.g., a combination of drugs delivered concomitantly, or in sequence. Some methods may comprise delivering sequential doses of the same agent to the subject. Variations of methods may comprise delivering multiple stimuli, e.g., a first optical stimulus and a second optical stimulus, in sequence with any intervening time interval, or in parallel. Certain variations of the methods may be used to treat a variety of conditions, with non-limiting examples including age-related macular degeneration, and other ocular diseases and conditions such as retinal and choroidal disease, cataracts, glaucoma, dry eye syndrome, optic neuropathy, orbital disease, corneal conditions, and uveitis. Some methods may be used to treat conditions not limited to the eye, such as cancer and diabetes.

Variations of the methods may comprise implanting a drug delivery device into a subject using any suitable technique, and into any appropriate anatomical area. For example, some methods may include implanting the drug delivery devices into an ocular region of the subject, e.g., the vitreous cavity, the retina, the sclera, the cornea, the conjunctiva, or any space or potential space within the orbit or eye itself. Some methods may comprise implanting multiple devices at multiple locations within the eye for treating more than one indication. In some variations, the methods may comprise implanting the drug delivery device into the vitreous cavity of the subject through an implantation site under the conjunctiva and sealing the implantation site after implantation by closing or pushing the conjunctiva over the implantation site. Implantation may be done subconjunctivally or sub-Tenon's layer, or in any intraocular, periocular, or orbital location. In some cases, the drug delivery devices may be implanted using a surgical incision or in combination with a vitrectomy procedure. In certain variations, the drug delivery devices may be implanted through a 20 gauge or smaller cannula. For example, the drug delivery devices may be implanted through a 21 gauge, a 22 gauge, a 23 gauge, a 25 gauge, or a 30 gauge or even smaller cannula.

Methods may comprise loading or reloading a drug reservoir of a device before or after the device has been implanted. Correspondingly, some methods may comprise implanting a sealable port that allows access to the drug delivery device after it has been implanted.

Any of the methods described above may comprise repositioning, retrieving, and or visualizing a device or a portion of a device. For example, some methods may include repositioning and/or retrieving a device using a tether or other feature (e.g., retrieval feature) affixed to a device. Of course, variations of the methods may comprise using other tools, e.g., forceps, clamps, hooks, or the like, for repositioning and/or retrieving drug delivery devices. Other methods may comprise implanting a drug delivery device that comprises one or more target regions that are configured to be visually differentiated. In some of these methods, reservoirs may comprise color-coded, shape-coded, and/or patterned target regions that allow or facilitate visual differentiation.

BRIEF DESCRIPTION OF THE FIGURES

FIGS. 6A and 6B show one example of a drug delivery device in which the formation of an orifice in a reservoir of the device releases an agent.

FIGS. 7A and 7B illustrate an example of a drug delivery device in which the exposure of a permeable or semi-permeable layer releases an agent from a reservoir.

FIGS. 10B to 10D illustrate an exemplary open loop system and FIGS. 10E to 10G illustrate an exemplary closed loop system.

FIGS. 13A to 13C show additional variations of housing configurations of an implant.

DETAILED DESCRIPTION

Figure 1A:
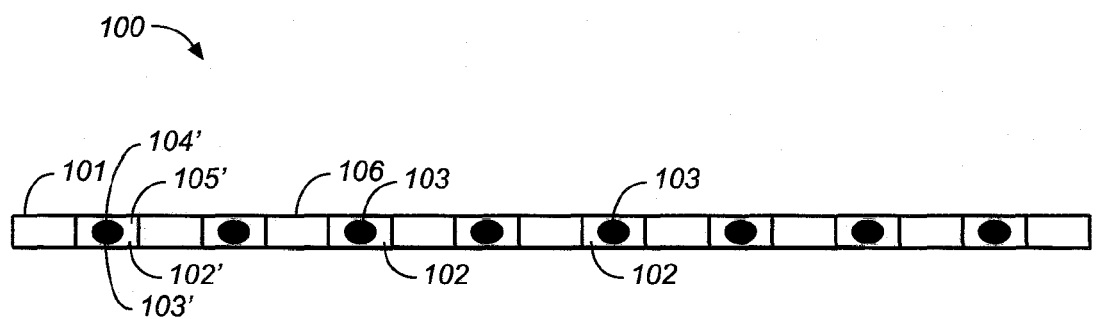
FIGS. 1A and 1B illustrate an exemplary drug delivery device in a straightened configuration and a curved configuration, respectively.

Described here are drug delivery devices, kits comprising such devices, methods of using the devices, and methods for loading the devices with an agent. The devices may be configured for use in a variety of locations within the body, and for a variety of applications. In general, the drug delivery devices may be configured for implantation into a subject, e.g., into an ocular region of the subject. The devices may comprise multiple reservoirs, each configured to be loaded with an agent. Reservoirs within devices may be configured to selectively respond to various triggers, thereby allowing selective, controlled release of one or more agents from one or more drug reservoirs in the devices to a desired anatomical region of the subject. Thus, the devices may be able to maintain an agent in active form and keep it sequestered within a drug reservoir until needed. Some drug delivery devices may be configured for controlled delivery of multiple drugs to provide combination drug regimens. Alternatively, or in addition, drug delivery devices may be configured for controlled delivery of sequential doses of the same or different drugs to provide extended drug therapies. Thus, the drug delivery devices may provide for long term (e.g., weeks, months, or years) drug regimens without the need for repeated invasive surgical procedures.

In addition to functioning as therapeutic devices, e.g., by delivering drugs, energy, etc., the devices described herein may also be configured to include features capable of performing diagnostic operations. For example, the devices may include features that are configured to perform single or multiple assays of target tissues or tissues or areas adjacent to the devices. In some variations, the diagnostic feature includes one or more sensors for detecting one or many physiologic parameters or environmental conditions of interest. The sensors may also emit a signal based on the sensed parameter or condition to directly or indirectly initiate therapy.

I. Devices

In general, the drug delivery devices are configured to be implanted into a subject. The devices may comprise one or more reservoirs, each configured to be loaded with an agent. As discussed in more detail below, the reservoirs may be preloaded with a drug, or loaded by a clinician or other user. Of course, a single drug reservoir may comprise more than one drug. If a single reservoir comprises more than one drug, the drugs may be released simultaneously, with different rates, or separately.

As previously stated, the reservoir may release one or more drugs after being triggered by a stimulus. Any suitable stimulus may be employed. For example, the stimulus may be optical, mechanical, chemical, electrical, magnetic, acoustic (e.g., ultrasound), radiofrequency, other radiative (e.g., ionizing radiation), and/or thermal in nature. Once triggered, the reservoir may release a drug contained therein in any suitable manner. For example, the drug may be released actively by an active mechanism (e.g., by a pump, injector, etc.) or passively (e.g., by diffusion, dissolution, polymer erosion, etc.).

After triggering a reservoir to release a drug, the drug may be released according to any suitable release profile. For example, continuous release, pulsed release, burst release (i.e., large initial release), bolus release (i.e., the entire reservoir is emptied immediately following triggering by a stimulus), or zero-order release profiles may be useful. Other modified drug release profiles are also contemplated. For example, the reservoirs may be configured for controlled release (i.e., controlled rate of release over an extended time period) or sustained release (i.e., slow release of drug over time, but not necessarily controlled release) of drugs.

The devices may comprise any number and combination of reservoirs. For example, they may comprise one, two, three, four, five, six, seven, eight, nine, ten, fifteen, or twenty or more reservoirs. When multiple reservoirs are employed, they may be individually or group-wise selectively triggered to release one or more drugs. For example, a first reservoir or group of reservoirs in a device may respond to a first stimulus, whereas a second reservoir or group of reservoirs does not, and the second reservoir or group of reservoirs may respond to a second stimulus, whereas the first reservoir or group of reservoirs does not. The selective triggering of multiple active reservoirs within a device may be carried out in any order, simultaneously, or with any suitable intervening time interval.

The devices may also be configured to include a diagnostic portion in addition to a therapeutic portion that, for example, releases one or more drugs or delivers energy. The therapeutic and diagnostic functionalities may be included in the devices to form either an open or a closed loop system. In an open loop system, the diagnostic portion may include a diagnostic feature that produces a signal that indirectly triggers a therapeutic function. For example, after a diagnostic operation is completed by the diagnostic feature that identifies target tissue, the diagnostic feature may emit or display a signal that is detected outside the body by a user (observer), e.g., a physician. The detected signal may indicate to the user to activate the therapeutic portion of the device to provide treatment. Alternatively, the emitted signal may be detected by the patient. When a closed loop system is employed, the same steps involved in an open loop system occur, but the therapeutic portion of the device is directly triggered to provide a therapeutic function by the emitted signal. A more detailed description of how such dual function devices may be used in an open or a closed loop system is provided below.

A. Device Configurations

The drug delivery devices may have any configuration, geometry, and/or dimensions that are suitable for their intended area or areas of use. For example, devices may comprise a unitary body that comprises one or more reservoirs, or they may comprise multiple body sections that each may comprise one or more drug reservoirs. Some variations of devices comprise body sections that contain no drug reservoirs, e.g., body sections for anchoring, visualization, and/or some other auxiliary purpose. In variations comprising multiple body sections, the body sections may or may not be interconnected. In many instances, devices may be at least partially flexible to assist the devices in conforming to a subject's anatomy, e.g., the vitreous cavity in an eye. For example, a device may comprise a flexible body, or relatively rigid device body sections that may, for example, be interconnected with flexible members. A drug delivery device for use in the eye may be designed for implantation into the vitreous cavity, the retina, the sclera, the cornea, the conjunctiva, or any space or potential space within the orbit or eye itself. For example, if a device is to be implanted in the vitreous, the device may have dimensions such that the device will not reach the retinal tissue or the lens to reduce the probability of interference with vision and/or injury to those areas.

Multiple reservoirs within a device may have any suitable configuration. For example, reservoirs may be distributed along a length, width, and/or around a circumference of a device body. Reservoirs may be arranged in any type of array, e.g., a linear array, a two-dimensional array, or a three-dimensional array. In other variations, devices may comprise reservoirs that are not arranged within a single device body, but instead are in separate body sections. In these instances, the reservoirs may be arranged within multiple device body sections that may or may not be coupled together.

Within a device, the reservoirs themselves may have a variety of configurations. For example, the reservoirs may comprise open, hollow volumes within device bodies, or they may comprise one or more plugs, replacement reservoirs, or the like inserted into device bodies. The reservoirs may have the same or different sizes and/or shapes within the same device. For example, a device body may comprise multiple similar or equally-sized sections, where single ones of these sections may be used to form some reservoirs, and multiple ones of these sections may be joined together to form a reservoir that is larger than other reservoirs in the same device. Adjacent reservoirs may be separated from each other using any suitable type of separation member. For example, reservoirs may be separated by an impenetrable barrier (e.g., a solid wall), a penetrable barrier, or a valve (e.g., a one-way valve that allows the reservoir to be loaded, but prevents backwards flow out of the reservoir). For example, reservoirs may be separated with a self-sealing membrane that may be penetrated with a syringe, or a permeable or semi-permeable membrane if it is desirable for reservoir contents to move between reservoirs.

Further, reservoirs may comprise one or more caps devised for containing a drug within a reservoir. Caps may be part of the reservoir and closed or sealed following loading of the reservoir, or caps may be added and sealed after loading. In some variations, the caps may be formed from a single layer. In other variations, the caps may be formed from multiple layers. For example, some caps may comprise a permeable or semi-permeable layer overlaid by a solid layer. After an opening in the solid layer is created, a drug may diffuse through the permeable or semi-permeable layer therebeneath. A cap may also comprise one or more sections arranged across a transverse dimension of the cap, e.g., transversely across a top of a reservoir. For example, a cap on a reservoir may comprise a target region devised to respond to a stimulus to release the drug within that reservoir. These variations are described in more detail below.

Figure 1B:
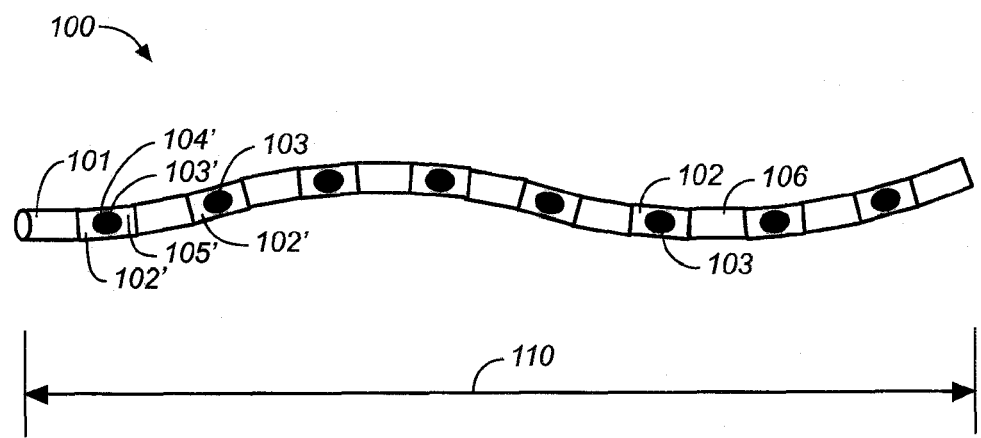

Referring now to the figures, an example of an elongated drug delivery device for implantation into an eye, e.g., the vitreous cavity of the eye, or any other space or potential space within the orbit or eye itself, is illustrated in FIGS. 1A and 1B. There, drug delivery device 100 comprises a device body 101 and multiple reservoirs 102. In this particular example, the reservoirs 102 are arranged in a linear array along the device body 101. The reservoirs 102 may be separated by separation members 106, which may comprise membranes, valves, and/or walls, as discussed above. If the device is to be implanted into the vitreous cavity, the dimensions of the device may be determined so that the device is not likely to enter the field of vision and/or damage the retinal tissues or lens area. Thus, elongated device 100 may, for example, have a length 110 that is at most about 1.0 cm, at most about 0.8 cm, at most about 0.6 cm, or at most about 0.5 cm. In other variations, the device may be about 3.5 mm or less in length. In yet further variations, the device may be about 1.0 mm or less in length. In the example shown in FIGS. 1A and 1B, each reservoir 102 in device 100 is configured to be loaded with an agent 103. Agents may be preloaded into the device, or loaded by a clinician or other user either before or after the device is implanted. Further, the device 100 has an elongated delivery configuration, which may fit into a cannula (e.g., a 20 gauge, a 21 gauge, a 23 gauge, a 25 gauge, a 30 gauge or even smaller cannula), as illustrated in FIG. 1A. A curved, implanted configuration is illustrated in FIG. 1B. Additional examples of devices comprising delivery and implanted configurations are described in more detail below.

Figure 2A:
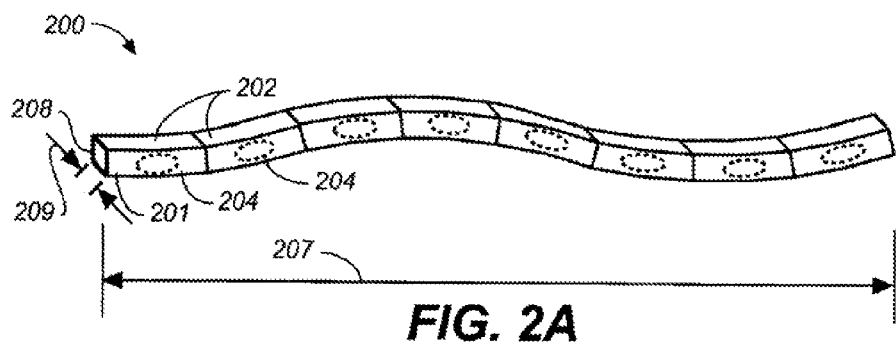
FIGS. 2A to 2F illustrate additional examples of drug delivery devices.

Although the particular device embodiment illustrated in FIGS. 1A and 1B is depicted as comprising a cylindrical cross-section, a linear array of reservoirs, and a unitary device body, other devices may have any suitable cross-sectional shape, unitary or multi-sectioned device bodies, and any distribution of reservoirs. For example, devices may have quadrilateral, ellipsoidal, polyhedral, or irregular cross-sections. Non-limiting examples of various combinations of device features are illustrated in FIGS. 2A to 2F. Referring first to FIG. 2A, device 200 comprises a flexible device body 201 that has a square or rectangular cross-sectional shape. The device body 201 may optionally comprise multiple body sections 202. The body sections 200 may be separated by a membrane, wall, or valve (not shown). The device 200 comprises one or more drug reservoirs 204, which may be distributed along a device length 207, along a device width 209, and/or around a device circumference 208.

Figure 2B:
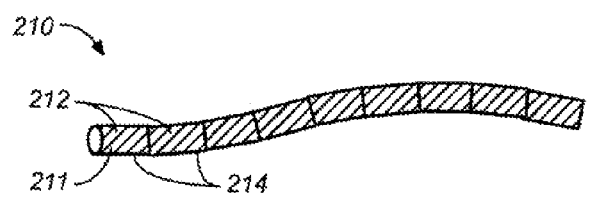
Figure 2C:
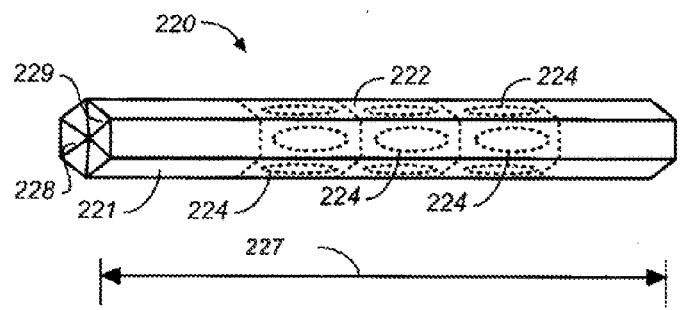

Referring now to FIG. 2B, device 210 comprises a cylinder-like device body 211 having an elliptical cross-section. The device 210 may comprise multiple body sections 212, which may be separated, e.g., by a membrane wall, or valve. The device 210 comprises one or more drug reservoirs 214. In this variation, the drug reservoirs 214 comprise a substantial part of the volume of body sections 212. Another variation of a device is shown in FIG. 2C. There, device 220 comprises a tubular device body 221 having a hexagonal cross-section. Here, again, the device body 221 may have multiple body sections 222. The device 220 comprises one or more drug reservoirs 224. In this variation, the drug reservoirs 224 are distributed both along a device length 227 and around a device circumference 228. Thus, in this particular embodiment, the reservoirs have a volume with a pie-shaped cross-section 229.

Figure 2D:
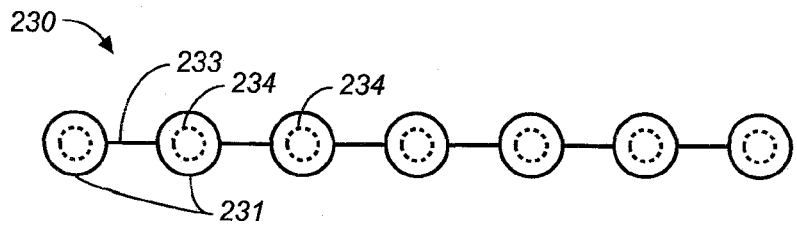

Devices may have a variety of arrangements of device body sections within a single device. For example, device body sections may be separate from each other, or they may be interconnected. In some variations, devices may have a chain-like or "string-of-pearls" configuration. An example of such a device is illustrated in FIG. 2D. There, device 230 has multiple body sections 231 connected together with one or more coupling elements 233, which may, for example, comprise one or more sutures. The body sections 231 may be fixedly or slidably coupled to the one or more coupling elements 233. The body sections 231 may have any suitable shape or combinations of shapes, e.g., spherical, ovoid, and/or cuboid. Each of the body sections 231 may comprise one or more drug reservoirs 234, or no drug reservoirs.

Figure 2E:
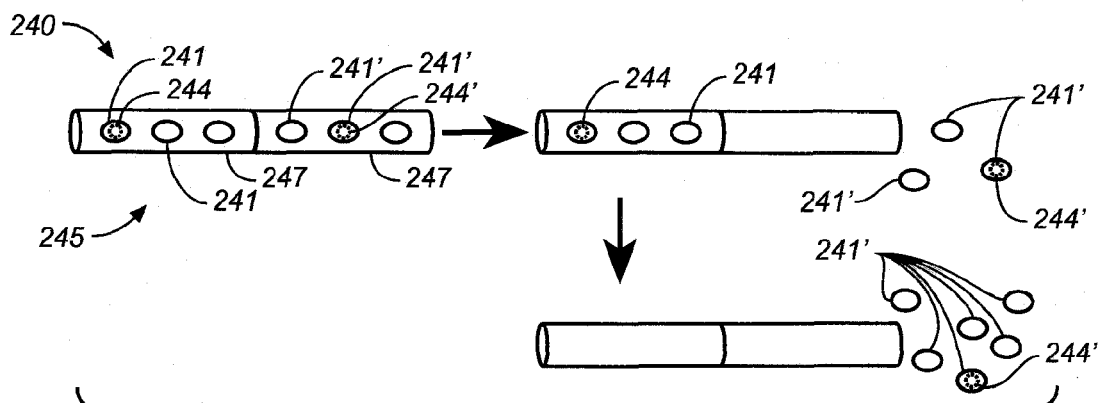
Figure 2F:
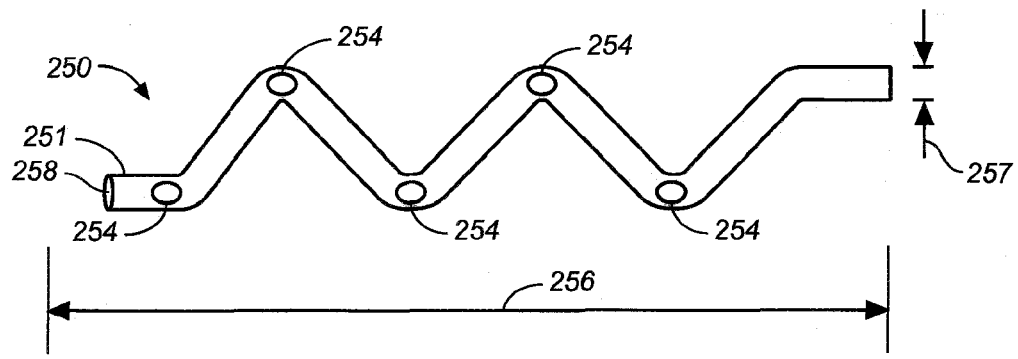

As stated above, devices may comprise multiple body sections that may be disconnected from each other. Referring now to FIG. 2E, device 240 comprises a housing element 245 that comprises multiple body sections 241 and 241'. Body sections 241 and 241' are not permanently coupled together, but rather may be released from housing element 245 upon implantation, e.g., to free-float in the vitreous or other part of the orbit or eye. As shown, housing element 245 may comprise multiple housing regions 247. Each housing region may be configured to release device body sections housed therein separately. Thus, for the example illustrated in FIG. 2E, body sections 241' may be released prior to body sections 241, or vice versa. Each of the body sections 241 and 241' may comprise one or more drug reservoirs 244 and 244', respectively. In some instances, a body section may comprise no drug reservoirs. A device such as that illustrated in FIG. 2E may be used to administer successive or sequential doses of a drug regimen, wherein the first dose is contained within reservoirs in body sections 241' and the second dose is contained within reservoirs in body sections 241. Still other variations of devices may comprise a bent, curved, helical, coiled, serpentine, zigzag-type, or other nonlinear type of device body structure. Referring now to FIG. 2F, device 250 comprises a device body 251 that at least partially follows a zigzag configuration. The device body 250 may comprise one or more drug reservoirs 254 distributed in any manner along a length 256, a width 257, and/or a circumference 258 of device body 251. Although the figures show the devices having certain numbers of reservoirs and having certain shapes, dimensions, geometries, configurations, etc., any suitable number of reservoirs may be included in the devices, and the devices may have any suitable shape, dimensions, geometry, and configuration. The devices may be shaped to fit inside the eye. Here the devices may have a first delivery configuration and a second implanted configuration, as further described below.

In other variations, the devices are configured to provide diagnostic functions in addition to therapy. Some variations of these dual function devices include the diagnostic features (e.g., sensors) and therapeutic features (e.g., reservoirs) on separate portions or regions of the device, but any configuration or organization of the features on the device may be employed. For example, the diagnostic features and therapeutic features may be located on discrete areas of the device or the features may not be structured in any organized fashion, but rather interspersed among each other on the device.

The diagnostic feature may be one or more assays or sensors, but is not so limited. Any assay or sensor suitable for implantation may be used. In some variations, the assays are configured to detect an analyte or detect an analyte as well as measure its level within a body tissue, fluid, space, etc. Non-limiting examples of analytes that may be detected include hemoglobin, glucose, inflammatory mediators such as VEGF and cytokines, photoreceptor factors, retinal pigment epithelium (RPE)-related factors, retinal factors, and drugs. Assays and sensors capable of detecting and/or measuring physiological parameters or environmental conditions of the eye may also be beneficial. For example, assays and sensors capable of detecting steroids, rapamycin, or alpha ($\alpha$)-VEGF in any ocular region, e.g., the vitreous cavity, the retina, the sclera, the cornea, the conjunctiva, or any space or potential space within the orbit or eye itself may be useful. Sensors that determine parameters such as intraocular pressure and blood pressure may also be useful.

Various types of sensors may also be included on the devices to perform diagnostic functions. For example, optical, thermal, electrical, mechanical, pressure, acoustic, magnetic, and chemical sensors may be used. Upon detecting a certain parameter or condition of the eye using a sensor, assay, or other diagnostic feature, the sensor, assay, other diagnostic feature, or diagnostic portion of the device may signal for therapy to be activated. For example, the signal may be binary, quantized, optical, acoustic, a color change of the device or area adjacent to or near the device, a shape change of the device, release of a substance (e.g., fluoroscein dye), energy emission, and movement of the device, e.g., by vibration. The signal may be detected by a user or observer such as a physician, the patient, a therapeutic portion of the device, or other devices, e.g., a wireless detector.

Figure 10A:
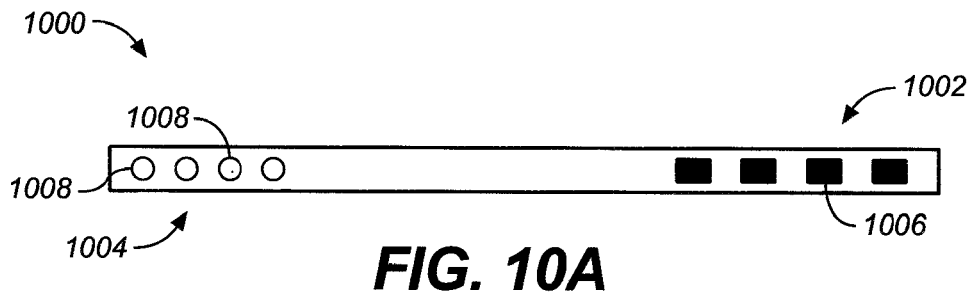
FIGS. 10A to 10G depict an exemplary drug delivery device comprising a diagnostic portion and a therapeutic portion and feedback systems using the device. In particular.

The dual function devices described here may form either an open or a closed loop system. In the variation shown in FIG. 10A, drug delivery device 1000 includes a therapeutic portion 1002 and a diagnostic portion 1004. Therapeutic portion 1002 may have one or more drug reservoirs 1006, as previously described. Diagnostic portion may include one or more diagnostic features such as sensors 1008, which are capable of detecting of a change in a physiological parameter or environmental condition and indicating that change. In one variation, the devices are designed to undergo a change in shape after injection or placement. In that particular embodiment, the shape change may be useful in optimizing positioning of the sensors and reservoirs to detect conditions and release drug, respectively, or to minimize visual interference or interference with other eye functions.

Figure 10B:
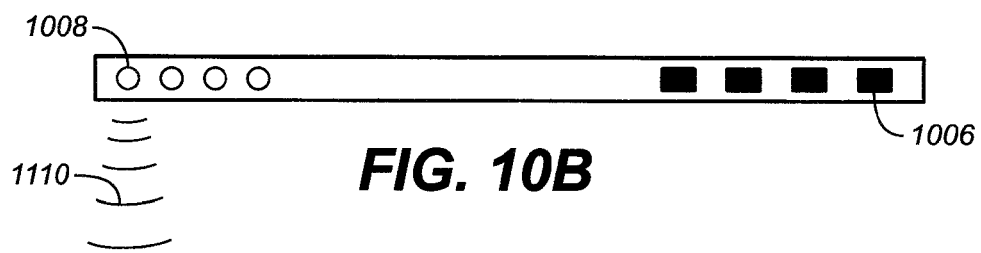
Figure 10C:
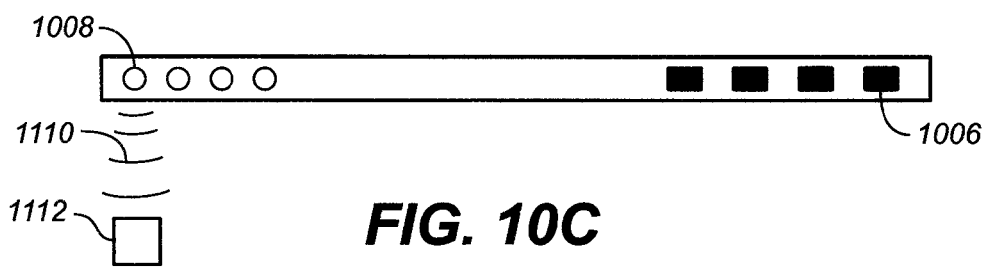
Figure 10D:
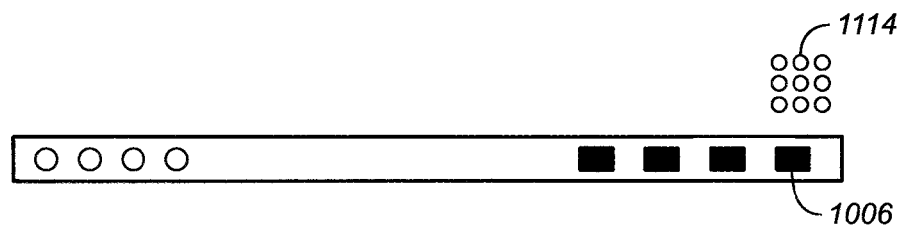
Figure 10E:
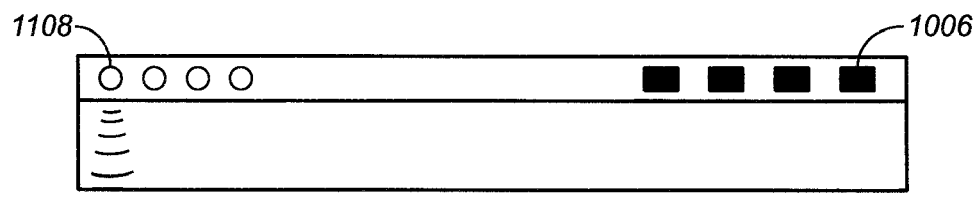
Figure 10F:
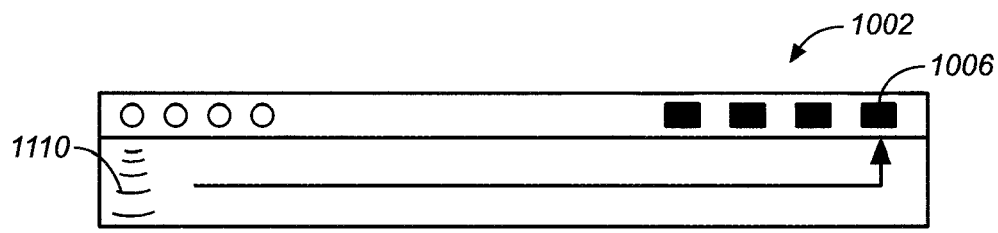
Figure 10G:
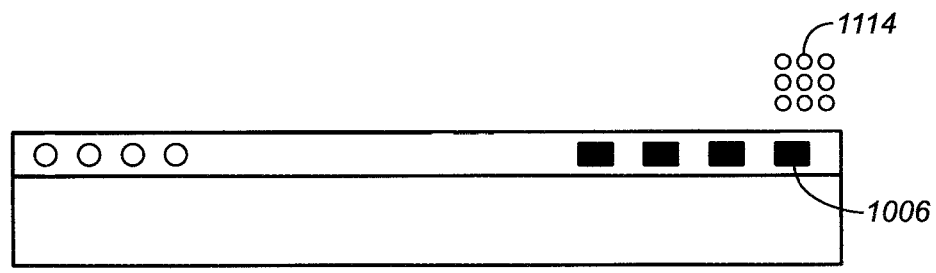

When employed in an open loop system, as illustrated in FIGS. 10B to 10D, sensor 1008 emits a signal 1110 when the parameter or condition of interest has been sensed (FIG. 10B). When signal 1110 has been detected by detector 1112 (FIG. 10C), this information is transferred to a user, e.g., a physician, who activates one or more reservoirs to deliver drug 1114 (FIG. 10D). Here the reservoir is indirectly triggered to release drug in response to the detected signal. For example, when an open loop system is used in the eye, the dual function devices may be configured to include a sensor that changes color upon detecting an increase in the level of VEGF. An ophthalmologist examining the eye with an ophthalmoscope would observe the color change and use another device to activate a reservoir on the device to release drug, e.g., anti ($\alpha$)-VEGF. When a closed loop system is used, as shown in FIGS. 10E to 10G, the sensor 1108 emits signal 1110 after detection of the parameter or condition of interest (FIG. 10E), but the reservoir 1006 on the therapeutic portion of the device 1002 is directly or automatically triggered (FIG. 10F) to release drug 1114 by the emitted signal 1110 (FIG. 10G).

The dimensions of the dual function devices described here will generally be determined based on the area of implantation. For example, a device for implantation in the eye should not interfere with the field of vision or cause damage to retinal tissues or the lens area. The dual function devices may, for example, have a length that is at most about 1.0 cm, at most about 0.8 cm, at most about 0.6 cm, or at most about 0.5 cm. In some variations, the dual function devices may be about 3.5 mm or about 1.0 mm or less in length. The devices may also be of any suitable cross-sectional shape. For example, they may be cylindrical, ellipsoidal, quadrilateral, polyhedral, or irregular in cross-section.

The dual function devices may be implanted using a cannula, generally, a 20 gauge or smaller cannula. For example, the dual function device may be implanted using a 21 gauge, a 22 gauge, a 23 gauge, a 25 gauge, or a 30 gauge or even smaller cannula. When used to implant devices within the eye, a 30 gauge cannula (needle) may be useful. The cannula may be used as an introducer to access the particular target area, tissue, space or potential space of the eye. For example, the devices may be implanted into the vitreous cavity, the retina, the sclera, the cornea, the conjunctiva, or the subconjunctival space. In some variations, the devices are placed on the outside surface of the eye. Some methods may involve incising the conjunctiva or Tenon's layer so that the implant can be placed subconjunctivally or sub-Tenon's layer. If applicable, the conjunctiva may then be closed or pushed over the incision. The device itself may be deployed from the cannula using a pusher, e.g., a wire or rod that is slidably received within the cannula, or a using a fluid, e.g., saline or a hyaluronic acid composition. In some variations, the cannula and/or pusher may be provided with markings to indicate how far they have been advanced.

Figure 3A:
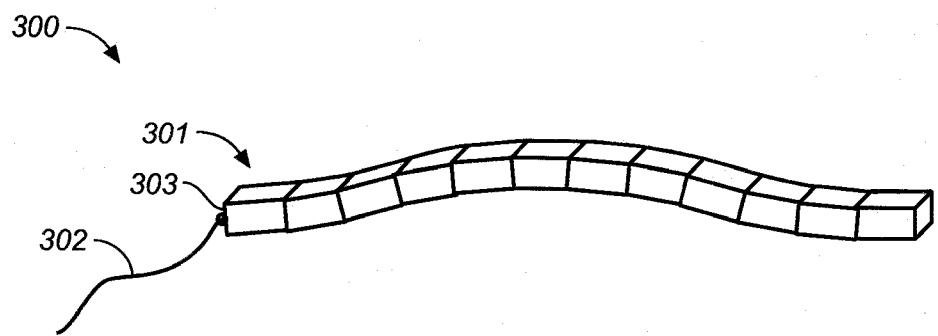
FIGS. 3A to 3C depict various embodiments of drug delivery devices comprising one or more tethers configured to position, retrieve, and/or secure the devices.
Figure 3B:
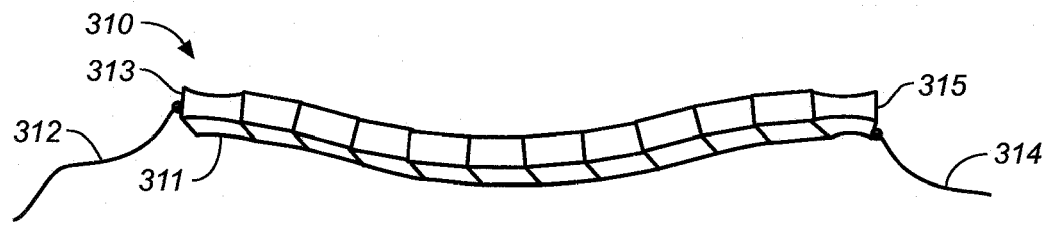

In some variations, the devices may comprise one or more tethers and/or other positioning features configured to allow retrieval of the device from the subject's anatomy, to allow repositioning of the device after it has been implanted in a subject, and/or to allow the device to be fixed to a portion of a subject's anatomy. Referring now to FIG. 3A, drug delivery device 300 comprises a tether 302 affixed to a proximal end 303 of device body 301. Tethers and/or other positioning features need not be affixed to an end of a device, but may be affixed to any part of a device body. Tethers and/or other positioning features may be made of any suitable material, e.g., a suture. Some variations of devices may comprise more than one tether and/or positioning feature, or a single tether or positioning feature that is fixed to the device at more than one position, e.g., at two different positions. Referring now to FIG. 3B, device 310 comprises tethers 312 and 314 affixed to opposite ends 313 and 315, respectively, of device body 311. In this variation of a drug delivery device, tethers 312 and 314 may be used to pull device 310 in generally opposing directions to position, move, and/or secure device 310.

Figure 3C:
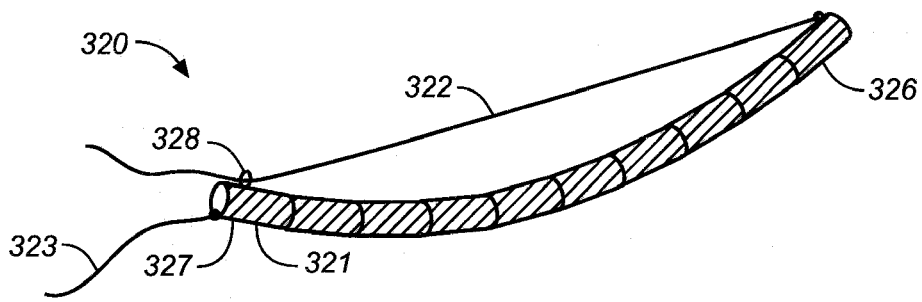

Tethers or other positioning features may also be used in some configurations to at least partially control the curvature of a device while implanted. Referring now to FIG. 3C, device 320 comprises tether 322 that is affixed to distal end 326 of device body 321. Tether 322 is threaded through a hole or loop 328 that is located on proximal end 327 of device body 321. Thus, when tether 322 is pulled proximally, distal end 326 may curl toward proximal end 327. To straighten device body 321, tether 322 may be allowed to go slack. Alternatively, another tether (not shown) may be affixed to the distal end 326 and threaded through another hole or hoop (not shown) located on proximal end 327. Tension applied to this additional tether may be used to apply force opposing the force supplied by tether 322 to straighten device body 321. Tether 323 may be affixed to proximal end 327 to position, secure, and/or remove device 320. In any of the variations of devices comprising a tether or other positioning feature, the tether and/or other positioning feature may be threaded out to an accessible point of the subject's anatomy. For example, for devices implanted in an eye, a tether and/or other positioning feature may be fed to the exterior of the eye by passing the tether underneath the conjunctiva. In other variations of devices implanted in an eye, a tether and/or other positioning feature may be attached, e.g., sewed in, e.g., to the sclera, to secure the device.

As stated above, variations of devices may also comprise positioning features or attachments in addition to, or instead of, tethers to position the devices within the anatomy and/or to secure the devices to the subject's anatomy. Such positioning features or attachments may comprise sutures, hooks, eyelets, staples, anchors, adhesives, and/or the like. Attachments may be devised to be relatively permanent, or temporary, e.g., biodegradable sutures, staples, and/or adhesives.

In some variations, the drug delivery devices described here may comprise a first delivery configuration and a second implanted configuration. For example, a drug delivery device may, in some circumstances, be configured to be implanted in the patient through a 20 gauge or a smaller cannula, e.g., a 21, gauge, a 22 gauge, a 23 gauge, a 25 gauge, or a 30 gauge or smaller cannula. Delivery configurations may be elongated, compressed, and/or folded, for example, while implanted configurations may be expanded, at least partially unfolded, and/or curved. Implanted configurations that are expanded relative to a delivery configuration may be expanded in one, two, or three dimensions. For example, a delivery configuration may be elongated, while its corresponding implanted configuration may be expanded to comprise at least one region comprising a curve, turn, or bend. In other variations, devices may be at least partially made of a shape memory material so that heat (e.g., from the subject's body) may cause the shape memory portion of the device to convert a device from its delivery configuration to its implanted configuration. Non-limiting examples of suitable shape memory materials that may be used include shape memory alloys such as Nitinol, and shape memory polymers such as oligo($\epsilon$-caprolactone)dimethacrylates and n-butyl acrylate.

Figure 4A:
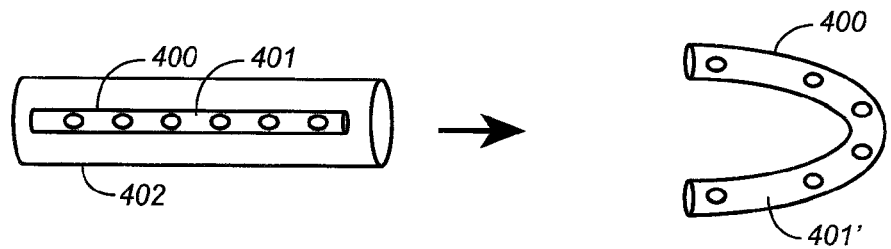
FIGS. 4A to 4D illustrate various examples of drug delivery devices comprising delivery configurations and corresponding implanted configurations.
Figure 4B:
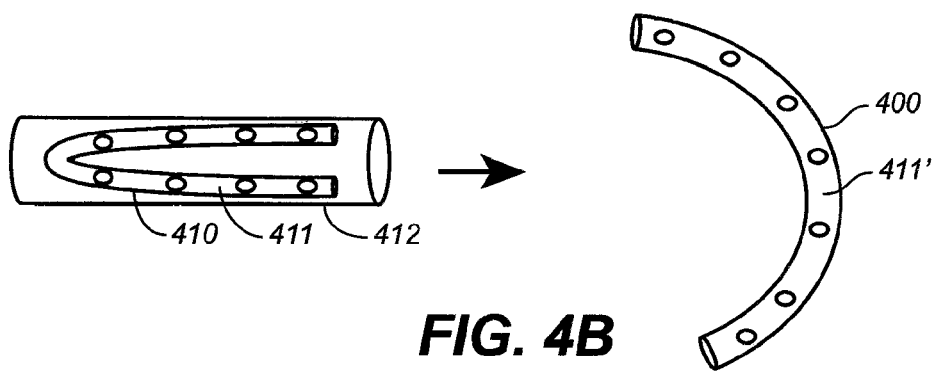
Figure 4C:
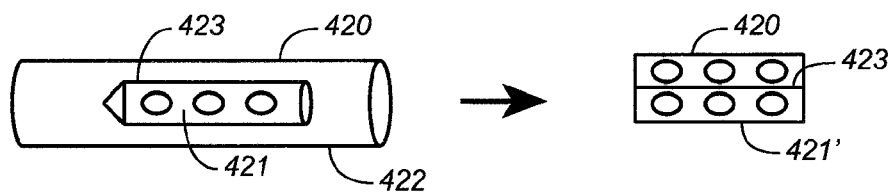
Figure 4D:
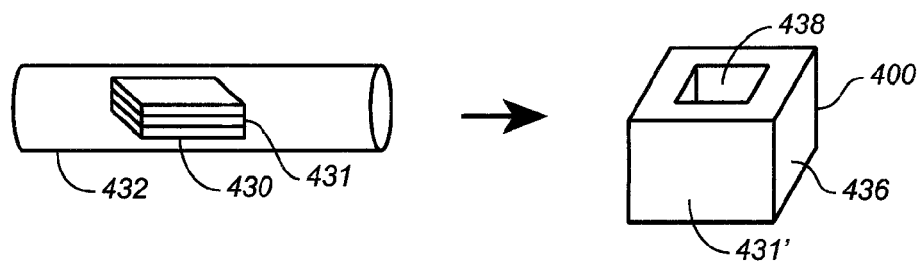

Exemplary delivery and implanted configurations for a variety of devices are shown in FIGS. 4A to 4D. In FIG. 4A, device 400 comprises an elongated delivery configuration 401 that, in this particular example, fits into a cannula 402. As shown, implanted configuration 401' may comprise at least one turn or bend. In some of these devices, implanted configuration 401' may comprise multiple turns or bends. Such devices may be at least partially made of a shape memory material, e.g., a shape memory alloy or a shape memory polymer, to trigger the configuration change. Referring now to FIG. 4B, device 410 comprises a compressed delivery configuration 411 that may fit into cannula 412. Upon implantation, device 410 may adopt an expanded implanted configuration 411'. Although device 410 is shown in this example as having an open shape, other variations of devices may have a closed configuration. In FIG. 4C, device 420 in its delivery configuration 421 comprises at least one fold 423. In this example, the folded delivery configuration 421 fits into cannula 422. Upon implantation, at least one fold 423 may partially unfold, leading to expanded implanted configuration 421'. Although device 420 is depicted here with a single fold for simplicity of illustration, devices with more than one fold, e.g., devices folded in an accordion fashion, are contemplated. Further, although implanted device configuration 421' is depicted as having a generally rectangular cross-sectional shape, other variations of folded devices are contemplated that have a corresponding implanted configuration with a generally round or ovoid cross-sectional shape. FIG. 4D illustrates yet another variation of a device having a delivery configuration and an implanted configuration. There, device 430 comprises a compressed sheet-like configuration 431 that may be designed to fit into cannula 432. Upon implantation, device 430 may adopt an expanded three-dimensional configuration 431' (e.g., a box-like configuration). In these variations, the agents may be contained within reservoirs in one or more walls 436, or alternatively or in addition, one or more agents may be loaded into a volume 438 created upon expansion of the device 430 to its implanted configuration 431'. Any one of the cannulas shown in FIGS. 4A to 4D (402, 412, 422, or 432) may, for example, be a 20 gauge, a 21 gauge, a 22 gauge, a 25 gauge, or a 30 gauge or smaller cannula.

B. Materials for Making Devices

Drug delivery devices or portions thereof may be formed from any suitable biocompatible material or combination of biocompatible materials. For example, one or more biocompatible polymers may be used to make devices, or portions of devices, e.g., device bodies and/or reservoirs. For examples, devices may be at least partially made from silicone rubber or a silicone elastomer. Other devices may be made from biocompatible materials such as methylmethacrylate (MMA), polymethylmethacrylate (PMMA), polyethylmethacrylate (PEM), and other acrylic-based polymers; polyolefins such as polypropylene and polyethylene; vinyl acetates; polyvinylchlorides; polyurethanes; polyvinylpyrollidones; 2-pyrrolidones; polyacrylonitrile butadiene; polycarbonates; polyamides; fluoropolymers such as polytetrafluoroethylene (e.g., TEFLON™ polymer); polystyrenes; styrene acrylonitriles; cellulose acetate; acrylonitrile butadiene styrene; polymethylpentene; polysulfones; polyesters; polyimides; natural rubber; polyisobutylene rubber; polymethylstyrene; and copolymers and blends thereof. In addition, additives may be added to polymers and polymer blends to adjust their properties as desired. For example, a biocompatible plasticizer may be added to a polymer formulation used in at least a portion of a device to increase its flexibility and/or its permeability. In other instances, a biocompatible filler such as a particulate filler, fiber and/or mesh may be added to impart mechanical strength and or rigidity to a portion of a device.

As stated above, some variations of devices include a permeable or semi-permeable membrane or layer. Any suitable material may be used to form a permeable or semi-permeable membrane or layer in a device. Depending on the agent that will diffuse through the permeable or semi permeable membrane, non-limiting examples of suitable materials may include: polycarbonates, polyolefins, polyurethanes, acrylonitriles, polyvinyl chlorides, polyamides, polysulphones, polystyrenes, polyvinyl fluorides, polyvinyl alcohols, polyvinyl esters, polyvinyl butyrates, polyvinyl acetates, polyvinylidene chlorides, polyvinylidene fluorides, polyimides, polyisoprenes, polyisobutylenes, polybutadienes, polyethers, polytetrafluoroethylene, polychloroethers, polymethylmethacrylates, cellulose, gelatin, silicone rubbers, other porous rubbers, and blends and copolymers thereof. Of course, the permeability of polymeric layers may be varied or tuned using mechanical techniques, e.g., by providing fine features such as perforations in a layer, by selecting a thickness of a layer, or by forming a mesh.

Some variations of devices may comprise one or more biodegradable polymers. A biodegradable polymer may be used as part of a device, e.g., as a reservoir wall or cap that is configured to passively release an agent contained in the reservoir. Alternatively, or in addition, a biodegradable polymer may be used as a matrix or casing comprising an agent, so that delivery of the agent may be at least in part controlled by degradation of the matrix or casing. Biodegradable polymers may also be used to configure devices having device bodies that erode over extended periods of time, e.g., over at least about six months, or over at least about one year or more. In this instance, the duration of drug release from the reservoirs may be shorter than the time it takes for the device body to degrade. In order to achieve this extended period of degradation, any number of biodegradable polymers or subtypes, combinations, blending, or crosslinking thereof may be used.

Non-limiting examples of suitable biodegradable polymers include alginate, cellulose and ester, collagen, dextran, elastin, fibrin, polysaccharides, hyaluronic acid, polyacetal, polyacrylates (L-tyrosine-derived or free acid), poly(β-hydroxyesters), polyamides, poly(amino acid), polyalkanotes, polyalkylene alkylates, polyalkylene oxylates, polyalkylene succinates, polyanhydrides, polyanhydride esters, polyaspartimic acid, polylactic acid, polybutylene digloclate, poly(caprolactone), poly(caprolactone)/poly(ethylene glycol) copolymers, polycarbone, L-tyrosin-derived polycarbonates, polycyanoacrylates, polydihydropyrans, poly(dioxanone), poly-p-dioxanone, poly(ϵ-caprolactone-dimethyltrimethylene carbonate), poly(esteramide), polyesters, aliphatic polyesters, poly(etherester), polyethylene glycol/poly(orthoester) copolymers, poly(glutarunic acid), poly(glycolic acid), poly(glycolide), poly(glycolide)/poly(ethylene glycol) copolymers, poly(lactide), poly(lactide-co-caprolactone), poly(DL-lactide-co-glycolide), poly(lactide-co-glycolide)/poly(ethylene glycol) copolymers, poly(lactide)poly(ethylene glycol) copolymers, polypeptides, polyphosphazenes, polyphosphesters, polyphophoester urethanes, poly(propylene fumarate-co-ethylene glycol), poly(trimethylene carbone), polytyrosine carbonate, polyurethane, PorLastin or silk-elastin polymers, spider silk, tephaflex, terpolymer (copolymers of glycolide lactide or dimethyltrimethylene carbonate), and combinations, mixtures or copolymers thereof.

C. Drugs for Delivery by Devices

The drug delivery devices may be configured to deliver any suitable drug or combination of drugs to a subject. It should be understood that the terms "drug" and "agent" are used interchangeably herein throughout. Drugs and agents may be for example therapeutic or diagnostic in nature. Diagnostic agents may be used as indicators for the presence or amount of a substance, which may in turn be an indicator of a condition or extent of disease. Non-limiting examples of diagnostic agents include contrast agents for imaging techniques such as ultrasound, magnetic resonance imaging, computed tomography, positron emission tomography, electron spin resonance, and optical imaging (e.g., fluorescence imaging). Therapeutic agents may be selected from the classes of agents including anti-inflammatories (e.g., steroidal and non-steroidal), anti-infectives (e.g., antibiotics, antifungals, antiparasitics, antivirals, and antiseptics), anti-allergens, cholinergic antagonists and agonists, adrenergic antagonists and agonists, anti-glaucoma agents, neuroprotection agents, agents for cataract prevention or treatment, antioxidants, antihistamines, anti-platelet agents, anticoagulants, antithrombics, anti-scarring agents, anti-proliferatives, antitumor agents, complement inhibitors (e.g., anti-C5 agents, including anti-C5a and anti-C5b agents), decongestants, healing promoters, vitamins (e.g., vitamin B and derivatives thereof, vitamin A, depaxapenthenol, and retinoic acid), growth factors, agents to inhibit growth factors (e.g., anti-growth agents), gene therapy vectors, chemotherapy agents, protein kinase inhibitors, small interfering RNAs, and combinations thereof. Non-limiting, specific examples of anti-growth agents include anti-vascular endothelial growth factor (VEGF) agents such as LUCENTIS™ (ranibizumab), AVASTIN™ (bevacizumab), vascular endothelial growth factor (VEGF) trap (aflibercept), and combinations thereof. Non-limiting, specific examples of drugs that may be used alone or as part of a combination drug therapy include LUCENTIS™ (ranibizumab), AVASTIN™

Avastin™ (bevacizumab), MACUGEN™ (pegaptanib), steroids, e.g., dexamethasone, triamcinolone, and fluocinolone, taxol-like drugs, vascular endothelial growth factor (VEGF) trap (aflibercept), anecortave acetate (RETAANE®), and limus family compounds. Non-limiting examples of members of the limus family of compounds include sirolimus (rapamycin) and its water soluble analog SDZ-RAD, tacrolimus, everolimus, pimecrolimus, zotarolimus, CCI-779 (Wyeth), AP23841 (Ariad), and ABT-578 (Abbott Laboratories) as well as analogs and derivatives thereof.

In devices comprising multiple reservoirs, the agents loaded therein may be the same or different. In some variations, multiple agents may be selected to be part of a combination drug therapy, e.g., a concomitant drug therapy that comprises the simultaneous delivery of multiple therapeutic agents and/or a sequential drug therapy that comprises the sequential delivery of multiple therapeutic agents. Devices may be configured to deliver sequential doses of the same drug by loading multiple reservoirs with the same drug, which may be unit doses, or different doses. For example, a device could be configured to hold multiple unit doses of Lucentis™ to be actively released over time, or a combination of multiple doses of Lucentis™ and one or more doses of steroids to be given in an appropriate combination as determined by the activating user or physician.

D. Drug Release

As indicated above, reservoirs may be triggered to enable release of a drug therefrom. A variety of stimuli may be used to trigger drug release from the reservoirs, including, but not limited to optical, radiofrequency, other radiative (e.g., ionizing radiation), mechanical, chemical, electrical, electromagnetic, acoustic (e.g., ultrasound), thermal, and magnetic stimuli, and combinations thereof. Subsequent to triggering of the reservoir, release of the drug contained therein may occur actively by an active mechanism (e.g., a pump, injector, etc.) or passively (e.g., by diffusion or dissolution). The release profile of the drug itself may then be of any suitable type. For example, the devices may be configured to release a drug according to a continuous release, pulsed release, burst release (i.e., large initial release), bolus release (i.e., entire reservoir emptied immediately following being triggered by a stimulus), or zero-order release profiles. Other modified drug release profiles are also contemplated. For example, the reservoirs may be configured for controlled release (i.e., controlled rate of release over an extended time period) or sustained release (i.e., slow release over time, but not necessarily at a controlled rate of release) of drugs.

In some applications, e.g., for delivering drugs to the eye, it may be desired to use an optical stimulus to trigger drug release from the reservoir. An optical stimulus may be very site specific, able to target a small spatial region, e.g., with a focused or relatively small spot-size beam, able to target a specifically shaped spatial region, e.g., through focusing and/or spatial filters, and may be tunable in terms of wavelength and power or energy density. Further, an optical stimulus requires no external lead, as may be required by an electrical stimulus or a mechanical stimulus. An optical stimulus is also relatively noninvasive, requiring no incision or injection. All of these factors may lead to reduced probability of damaging or affecting surrounding tissues when performing a procedure with an optical source such as a laser.

Some variations of drug delivery devices may comprise a first reservoir that is configured to be loaded with a first agent and a first target region. If present, the first target region on a reservoir may be configured to selectively respond to a first stimulus to trigger release of an agent from that reservoir. Target regions may have any suitable geometry and/or configuration. Further, target regions may be configured to selectively respond to any type of stimulus, e.g., an optical, radiofrequency, magnetic, chemical, thermal, electrical, and/or acoustic (e.g., ultrasound) stimulus. Ionizing radiation, e.g., beta-radiation or gamma-radiation, may be used. The target regions may comprise one or more discrete features, e.g., a feature with a well-defined geometry, such as a dot or square, an array of marks, a line, and/or the like, on a surface of a reservoir wall or cap. Target regions may, in some variations, be a different material from at least part of a reservoir. Target regions may be created on or applied to devices in any suitable manner, e.g., by painting, dipping, applying through a mask, selectively etching, or the like. In other variations, target regions may be more expansive and/or diffuse, e.g., they may comprise generally a surface, wall, cap, or other portion of a reservoir. Such target regions may be integrally formed with at least part of the reservoir, e.g., by doping one or more radiation absorbers for absorbing a stimulus having a frequency within a particular radiation frequency range into a reservoir wall and/or cap, or one or more magnetic materials into a reservoir wall and/or cap.

Figure 5A:
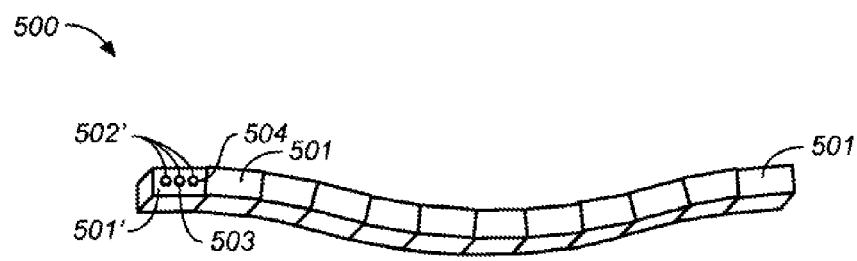
FIGS. 5A to 5C illustrate various examples of target regions of drug delivery devices.
Figure 5B:
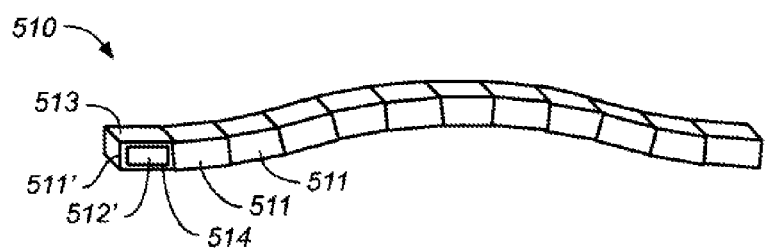
Figure 5C:
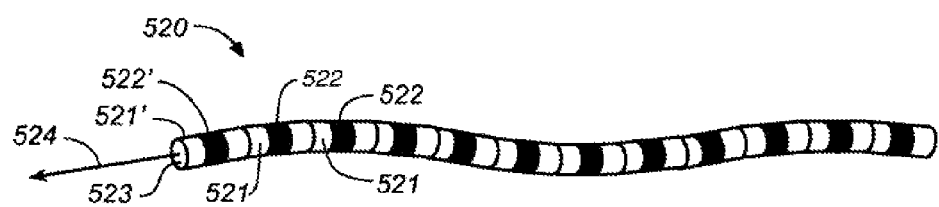

Some examples of devices comprising target regions are illustrated in FIGS. 5A to 5C. Referring first to FIG. 5A, drug delivery device 500 includes multiple reservoirs 501 that may each be configured to be loaded with an agent. A first reservoir 501' includes a first target region 502' and is configured to be loaded with a first agent. First target region 502' may be configured to selectively respond to a first stimulus, e.g., a first optical stimulus that selectively absorbs light over a first wavelength range. First target region 502' in this example may comprise one or more target features 503 (which may, for example, be discrete or separately identifiable features such as circular regions, slits, or the like) that are disposed on or part of a wall 504 of first reservoir 501'. Thus, when the first stimulus impinges upon the first target region 502' (e.g., light overlapping at least a portion of the first wavelength range is incident upon the target region), the interaction of the first stimulus with the first target region (e.g., absorption of light by the first target region if the first stimulus is optical), may trigger release of the first agent. It should be pointed out that other reservoirs 501 may or may not comprise target regions. For example, one or more reservoirs 501 may be configured to release one or more agents loaded therein in a passive manner. It should be pointed out that the reservoirs within a device may be configured to release one or more agents in any order, simultaneously, or with any suitable intervening time interval. For example, if one reservoir is configured for passive release of an agent, passive release of that agent may begin prior to, simultaneously with, or after active release of an agent from another reservoir.

In some variations of the devices, a target region on a single reservoir may be configured to respond to more than one stimulus. For example, referring back to FIG. 5A, one or more of the target features 503 that make up first target region 502' on first reservoir 501' may be configured to respond to separate stimuli. In some variations, the target features 503 may be stimulated (e.g., irradiated) sequentially to step-wise release a drug within reservoir 501'. This configuration may be chosen, e.g., for an adjustable rate flow of first agent out of the first reservoir 501'. In other variations, one or more target features 503 may comprise a different sensitizer (e.g., photosensitizer) than another of the target features 503 so that different stimuli (e.g., different wavelengths of light) may be required to cause release of first agent through stimulation of the different target features 503. In still other variations of the devices, a target region may comprise more than one layer, e.g., a first layer and a second layer. A first stimulus (e.g., a first optical stimulus) may be required to break or create an orifice or aperture in the first layer, and a second stimulus, which may or may not be optical, may be required to break the second layer to release the first agent to the subject.

In yet further variations using a layered target region, a first stimulus that creates an orifice in the first layer may cause the first agent to be slowly released from the reservoir. Upon breakage of the second layer with a second stimulus, which may or may not be optical, the first agent may be more rapidly released from the reservoir. Drug release from the reservoir may also be modified by the formation of a plurality or series of orifices in one or more layers, or changing the permeability of the material used to form the layers (e.g., by changing the molecular structure of the material).

Referring now to FIG. 5B, drug delivery device 510 comprises device body 513 comprising multiple reservoirs 511 that each may be configured to be loaded with an agent. In this particular example, first reservoir 511' is configured to be loaded with a first agent, and includes a first target region 512'. First target region 512' may be configured to selectively respond to a first stimulus, e.g., a first optical stimulus comprising the selective absorption of light over a first wavelength range, to trigger release of the first agent. In this variation, the first target region 512' may extend over a substantial amount of the surface area of reservoir wall 514, e.g., over about 25%, or over about 50%, or over about 75%, or over about 90% of the surface area of reservoir wall 514.

Referring now to FIG. 5C, drug delivery device 520 comprises an elongated cylindrical structure having an annular wall defining multiple reservoirs 521, each of which may be configured to be loaded with an agent. First reservoir 521' is configured to be loaded with a first agent, that when stimulated with a first stimulus, e.g., a first optical stimulus comprising light having a wavelength in a first wavelength range, causes release of the first agent from first reservoir 521'. In this variation, the first target region 522' extends circumferentially around the annular wall of the device body 523 about the first reservoir, so that even if the device 520 rotates around a longitudinal axis 524 after it has been implanted, e.g., if the device is allowed to float within a subject's vitreous or other space or potential space within the orbit or eye itself, an external stimulus may still be directed at the first target region 522', e.g., first target region 522' may still be irradiated with an external light source. Other reservoirs 521 within the same device also may comprise circumferentially-extending target regions 522, or other reservoirs may comprise target regions having other geometries or configurations. Circumferentially-extending target regions may extend around any suitable portion of a device's circumference, e.g., about 90 degrees, about 180 degrees, about 270 degrees, or about 360 degrees. Thus, an orifice may be created at any position around the circumference of the annular wall in the target region. The target region in these devices may be responsive to any source, but these devices may be particularly well-suited for use with externally directed stimuli that are aimed at the target region, e.g., a laser or other beam, e.g., by simplifying the alignment of the stimulus with the target region. In an embodiment, the device 520 is configured to release the first agent from the first reservoir 521' through an orifice created in the annular wall of the device body 523 at the first target region 522' upon application of the optical stimulus to the first target region 522'.

As stated above, some variations of devices may comprise a first reservoir comprising a first target region that is configured to selectively respond to a first optical stimulus. In these variations, the first optical stimulus may comprise irradiation of the first target region with a wavelength of light within a first wavelength region that is selectively absorbed by the first target region. For example, a chromophore that absorbs over the first wavelength region may be doped into at least a portion of the first target region. Referring back to FIGS. 1A and 1B, device 100 comprises first reservoir 102' that is configured to be loaded with a first agent 103'. Device 100 also may optionally comprise a first target region 104' that is on or part of a wall 105' of first reservoir 102'. First target region 104' may be configured to selectively respond to a first optical stimulus to release first agent 103' from reservoir 102'.

The first target region of the devices may be configured in any suitable manner to selectively absorb light over a first wavelength range. For example, the first target region may be configured to absorb light from a light source that is readily available to a clinician or other user, e.g., ophthalmic lasers used by clinicians or other users who specialize in the treatment of retinas. Such light sources include a diode laser (e.g., a diode laser emitting red or green light), a Nd:YAG laser, a Nd:YLF laser, a helium-neon laser, an argon ion laser, a krypton ion laser, a CuBr vapor laser, a pumped dye laser, or an excimer laser. Illustrative lasers may include argon ion lasers and Nd:YAG lasers, e.g., frequency-doubled Nd:YAG lasers. In other cases, light-emitting diodes or lamps may be used as light sources. The output of a light source may be filtered with one or more optical filters or other wavelength selection device to set a desired wavelength range. Light sources may be pulsed or continuous wave (CW). Non-limiting examples of pumped dye lasers include a pulsed dye laser pumped by a frequency-doubled Nd:YAG, a frequency-doubled Nd:YLF, or an excimer laser, and a continuous wave dye laser pumped by an argon ion laser. Thus, a retinal specialist may have one or more pulsed or CW lasers available for use that emits coherent light at discrete wavelengths ranging from about 100 nm to about 10,000 nm. For example, the wavelengths may range from about 500 nm to about 1500 nm, from about 500 nm to about 700 nm, or from about 500 nm to about 600 nm. In some variations, the wavelengths may range from about 1040 nm to about 1064 nm.

An optical stimulus may have any suitable energy or power density. In general, the energy or power density may be selected to trigger the release of an agent from a reservoir in a drug delivery device without damaging or substantially damaging surrounding tissues. For example, energy densities of about 0.01 J/m$^2$ or less to about 5 J/m$^2$ may be used, and/or power densities of about 0.01 W/cm$^2$ or less to about 50 W/cm$^2$ may be used. If a pulsed light source is used, repetition rates of about 1.0 Hz to about 2000 kHz may be used. In some variations, repetition rates of about 1.0 Hz to about 1.0 MHz may be used, e.g., about 1.0 Hz to about 20 Hz, or about 100 Hz to about 1.0 MHz, or about 500 Hz to about 1.0 MHz. Any suitable pulse duration may be used. For example, pulse widths of about 1.0 ns to about 1.0 ms may be used, e.g., about 1.0 ns to about 100 ns, or about 100 ns to about 500 ns, or about 500 ns to about 1.0 µs, or about 1.0 µs to about 50 µs, or about 50 µs to about 500 µs, or about 500 µs to about 1.0 ms. In some variations, shorter pulse widths may used. For example, the pulse width may range from about 200 femtoseconds to about 3000 femtoseconds. Any suitable spot size and/or shape may be used. For example, the spot size of the incident light may be adjusted, e.g., using a lens, a focusing mirror, and/or a spatial filter, to be approximately coincident with a target region to avoid unnecessary irradiation of surrounding areas. In some cases, the shape of an incident beam may be used as a selective trigger. For example, a reservoir may have a target region with a specific shape and/or size, e.g., a slit-shape, so that unless an incident beam is focused or otherwise adjusted to fit within or have sufficient overlap with the size and/or shape of the target region, insufficient power density may be incident on that target region to activate release of agent within the reservoir. Thus, incident beams used to activate reservoirs may have a variety of spot sizes and shapes. Incident beams may have a spot size and/or shape with at least one dimension that is in the range of, for example, about 1 μm to about 2000 μm (2.0 mm). In some instances, the incident beam may have a spot size and/or shape with at least one dimension that is about 200 μm, about 100 μm, or about 50 μm or less.

In some variations of the devices described here, the first target region may comprise a first photosensitizer or a first chromophore that is selected to absorb light in the first wavelength range. The first wavelength range of the first target region of some devices may overlap with emission from a desired optical source, which may comprise a laser, filtered output from a lamp, or a light-emitting diode. For example, the first wavelength range may overlap with an argon ion laser, a Nd:YAG laser, e.g., a frequency-doubled Nd:YAG laser, a diode laser (e.g., a diode laser emitting red or green light), a Nd:YLF laser, a krypton ion laser, a helium-neon laser, a CuBr vapor laser, a pumped dye laser, or an excimer laser. Chromophores that absorb over these wavelengths may be any suitable biocompatible chromophores. In addition, chromophores that are used in photodynamic therapy may be used. Non-limiting examples of such chromophores include phthalocyanines, porphyrins (e.g., hematoporphyrin, or hematoporphyrin derivative and protoporphyrin), and chlorins.

Some variations of the drug delivery devices described above that comprise at least one optically-triggerable reservoir may comprise additional reservoirs configured to be loaded with additional agents. For example, devices may comprise two reservoirs, where the first reservoir may deliver a first agent in response to a first optical stimulus, and the second reservoir may deliver a second agent in response to a second stimulus, which may or may not be optical in nature. For example, the second stimulus may comprise a thermal, radiofrequency, other radiative (e.g., ionizing radiation), electrical, acoustic (e.g., ultrasound), magnetic, chemical and/or mechanical stimulus. For example, delivery of the second agent from the second reservoir of these devices having a first optically-triggerable reservoir may be initiated by an electrical/thermal stimulus, where an electrical signal is applied to a resistive heating element to heat a portion of the reservoir to cause release of the second therapeutic agent. Any type or combination of additional stimuli may be used to initiate drug delivery from additional reservoirs. In devices with more than one reservoir, reservoirs may be configured to release agents in any order, simultaneously, or with any suitable intervening time interval.

Thus, some variations of drug delivery devices may comprise a first reservoir configured to release the first agent loaded therein in response to a first optical stimulus, and a second reservoir configured to release the second therapeutic agent loaded therein in response to a second optical stimulus. In these variations, the first optical stimulus may be the same or different from the second optical stimulus. If the first and second optical stimuli are different, they may be different in any respect. For example, in some variations the first optical stimulus may comprise irradiation of the drug delivery device with a first wavelength, and the second optical stimulus may comprise irradiation of the drug delivery device with a second wavelength. In certain variations, the first optical stimulus may comprise irradiation with a second power density, and the second optical stimulus may comprise irradiation of the device with a second power density. Devices may contain three or more reservoirs, and three or more different optical stimuli may be used to selectively release three or more therapeutic agents contained within the reservoirs. As stated above, stimulation of multiple reservoirs within a device may occur in any order, simultaneously, or with any suitable intervening time interval.

If a device comprises more than one reservoir, target regions of different reservoirs may comprise different chromophores that have non-overlapping or only partially overlapping absorption spectra. In some cases, chromophores used in different target regions may be selected to have well-separated absorption spectra with very little or no overlap. In some cases, a chromophore may be selected to reduce or minimize overlap of its absorption spectrum with native tissues, e.g., eye tissues, to reduce or minimize potential damage to native tissues. Some variations of the devices may have first and second reservoirs comprising first and second target regions, respectively. The first target region may comprise a first chromophore configured to absorb light having a first wavelength and the second target region may comprise a second chromophore configured to absorb light having a second wavelength. The absorption spectra of the first and second chromophores may be well-separated or only partially overlap, so that when the first target region comprising the first chromophore is irradiated with light of the second wavelength, little or no absorption occurs, and when the second target region comprising the second chromophore is irradiated with light of the first wavelength, little or no absorption occurs. Thus, the first and second reservoirs may be selectively and independently triggered using light of the first and second wavelengths, respectively. In some cases, the chromophores used in the target regions of the first and second reservoirs may be selected to have essentially non-overlapping absorption spectra in the region of interest to increase the selectivity between two or more reservoirs, i.e., to reduce the probability that an optical stimulus activates reservoirs not intended to be activated by that optical stimulus. Of course, this concept may be extended to drug delivery devices comprising more than two reservoirs, e.g., a third reservoir comprising a third target region configured to absorb light of a third wavelength. The third target region may comprise a third chromophore whose absorption spectrum does not substantially overlap the absorption spectra of the first and second chromophores. In some cases, the chromophores may absorb incident light by two-photon absorption, e.g., by the absorption of two photons of the same wavelength achieved by irradiating the target region with relatively high intensity light, or by the absorption of two photons of two different wavelengths achieved by simultaneously irradiating the target region with two light sources emitting the two different wavelengths.

The use of light of different wavelengths to selectively trigger release of drugs from multiple reservoirs, each configured to selectively absorb certain wavelengths of light, e.g., visible wavelengths, may also enable improved visualization for the clinician or other user. For example, target regions that are configured to absorb different wavelengths may be different colors, e.g., color-coded, to allow a clinician or other user to readily identify which reservoir to trigger, e.g., with a light beam and/or other stimulus. For example, color-coding may be used to identify one or more reservoirs containing a particular dose or a particular drug. In certain variations, color-coding may be used to identify a set of reservoirs in a device for a particular combination drug regimen, and/or to identify dose or drug to be used in a serially-delivered drug regimen. Other visualization schemes may be used to allow ready visual identification of devices and/or specific reservoirs within devices, such as shape-coding of target regions, or patterning of target regions, e.g., to comprise a certain number of target features, which may be discrete or separately identifiable features such as circular regions, slits, or the like. Color-coding, shape-coding and/or patterning of target regions may be used in any combination for visualization of reservoirs within a device, or between devices. In some variations, emission from an irradiated target region may aid visualization. For example, if a first target region in a first reservoir in a drug delivery device is configured to selectively absorb green light, the clinician or other user may be able to align the green light source with the first target region by observing emission, e.g., fluorescence, from the first target region when green light is incident thereon. Cutoff filters and the like may be used to aid in the visualization of such emission when a target region absorbs incident light. Further, if a second reservoir in the same drug delivery device is configured to selectively absorb red light, the clinician or other user may be able to differentiate between the first and second reservoirs by their selective absorptions of visible light.

For devices comprising optically-triggerable reservoirs that include one or more target regions responsive to optical stimuli, the target regions may have any suitable geometry or configuration. As described above, target regions may comprise discrete or diffuse features, and may, in some variations, be a different material from at least part of a reservoir. Target regions may be created or applied in any manner, e.g., by painting onto a reservoir or cap, dipping at least part of a reservoir or cap, patterning through a mask or with selective etching, or the like. In some variations, one or more target regions may be integrally formed with at least part of a reservoir, e.g., by doping one or more chromophores into a portion of a reservoir wall or cap.

The release of the first agent triggered by the first optical stimulus may be accomplished by any one of a variety of drug release schemes, or a combination of drug release schemes. For example, absorption of light by the first target region may, in some variations of devices, trigger a reservoir to release the first agent by causing the formation of a first orifice in a reservoir wall or cap, or the formation of more than one orifice in the reservoir wall or cap. One such example is illustrated in FIGS. 6A and 6B. There, device 600 comprises reservoir 601. Reservoir 601 is configured to contain agent 604 therein. Reservoir 601 may comprise walls 602 and an impermeable layer 603 that may function as a cap. Layer 603 may comprise a first target region 605 that selectively absorbs the incident light 606. Target region 605 may be disposed anywhere within layer 603, e.g., near a wall 602, or towards a transverse central region of layer 603. As illustrated in FIG. 6B, the selective absorption of incident light 606 by target region 605 may cause the formation of an orifice 608 through which an agent may be delivered. Thus, selective and controllable release of agent 604 may be achieved.

In other variations, the one or more orifices formed by an optical stimulus may expose a second permeable or semi-permeable layer. In these variations, the first optical stimulus may initiate diffusion-controlled delivery of the first agent through the exposed permeable or semi-permeable layer. A variation of such a device is illustrated in FIGS. 7A and 7B. There, device 700 comprises reservoir 701. Reservoir 701, in turn, stores agent 704. Reservoir 701 may comprise walls 702, a permeable or semi-permeable layer 710, and an impermeable layer 703 overlaid on layer 710. Impermeable layer 703 may comprise a target region 705 that selectively absorbs the incident light 706. As illustrated in FIG. 7B, the selective absorption of incident light 706 by target region 705 may at least partially expose layer 710, so that agent 704 can diffuse through layer 710. In other variations, the one or more orifices formed by an optical stimulus may expose a second drug release control mechanism or device, e.g., a biodegradable capsule or matrix.

In still other variations, one or more orifices formed by an optical stimulus may expose an additional housing or other feature that is responsive to yet another stimulus, e.g., a thermal stimulus (such as body heat), a chemical stimulus (e.g., pH or a receptor responsive to a certain chemical species), or the like. For example, an optical stimulus may reveal a polymer gel or network that undergoes a volumetric change in response to an environmental stimulus to release a drug contained within that gel. Variations of such polymer gels may include interpenetrating polymer networks (IPNs) or semi-interpenetrating polymer networks (SPNs) comprising cross-linked networks of natural and/or synthetic hydrogels. Variations of IPNS and SPNs that may be used to make drug delivery housings or contains may, in some variations, include poly(vinyl alcohol, gelatin, cellulose, and poly(N-isopropylacrylamide. Non-limiting specific examples include gelatin/cellulose networks, poly(vinyl alcohol)/poly (N-isopropylacrylamide) networks, and hyaluronic acid/poly (vinyl alcohol) networks.

In some variations of the devices described here, an optical stimulus may result in a shape change of at least part of the reservoir to initiate drug delivery. For example, an optical stimulus may cause at least a portion of a reservoir wall or cap to become thinner, thereby increasing its permeability. In other variations, at least a portion of a reservoir wall or cap may comprise a shape memory material, e.g., a shape memory polymer, so that absorption of light from an optical stimulus may cause local heating which, in turn, induces a change in the shape memory portion of the reservoir, leading to rupture of a portion of the reservoir to deliver the first agent. Non-limiting examples of shape memory polymers that may be used in those variations of devices include oligo(ε-caprolactone)dimethacrylates and n-butyl acrylate. In devices comprising caps, the delivery of an optical stimulus to the first target region of the device may cause one or more dimensions of the reservoir to change, leading to rupture or leaking of the cap.

The drug delivery devices described here may have a variety of applications. For example, they may be configured to treat a variety of conditions. Some devices may be configured to treat age-related macular degeneration, whereas other devices may be configured to treat diabetes, cancer, glaucoma, cataracts, retinal and choroidal disease, dry eye syndrome, optic neuropathy, orbital disease, corneal conditions, uveitis, and other conditions. The devices may be particularly well-suited to treating chronic conditions or other conditions that require multiple administrations of agents over extended periods of time. Because they allow storage of agents within reservoirs and provide an "on-demand" delivery scheme, the devices may allow extended treatments and reduce or eliminate the need for repeated invasive procedures. In addition, the "on-demand" delivery schemes of the drug delivery devices may allow a single configuration of a device to be used for multiple types of subjects, e.g., by adjusting the loading of the reservoirs. Further, the devices may allow for adjustment of a treatment regimen even after the device has been implanted without the need for surgical intervention. Some variations or combinations of the devices may be useful for multiple different indications. For example, a single device may be loaded with different drugs for multiple indications, and/or multiple devices may be implanted for multiple indications.

Figure 8A:
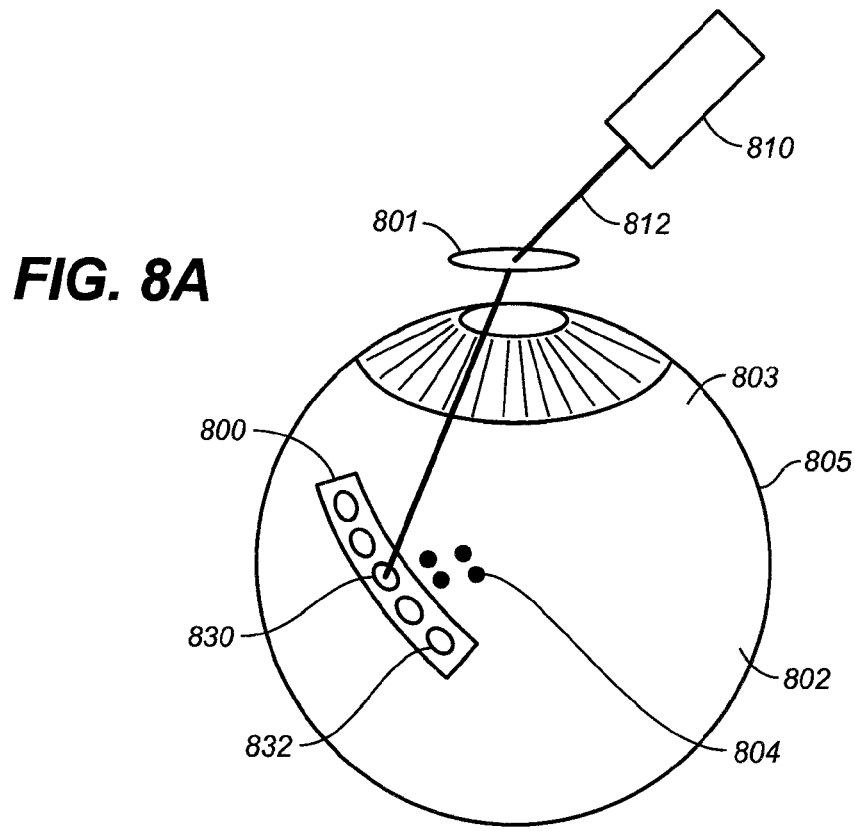
FIGS. 8A and 8B illustrate one variation of a drug delivery device that has been implanted into the vitreous cavity of an eye.
Figure 8B:
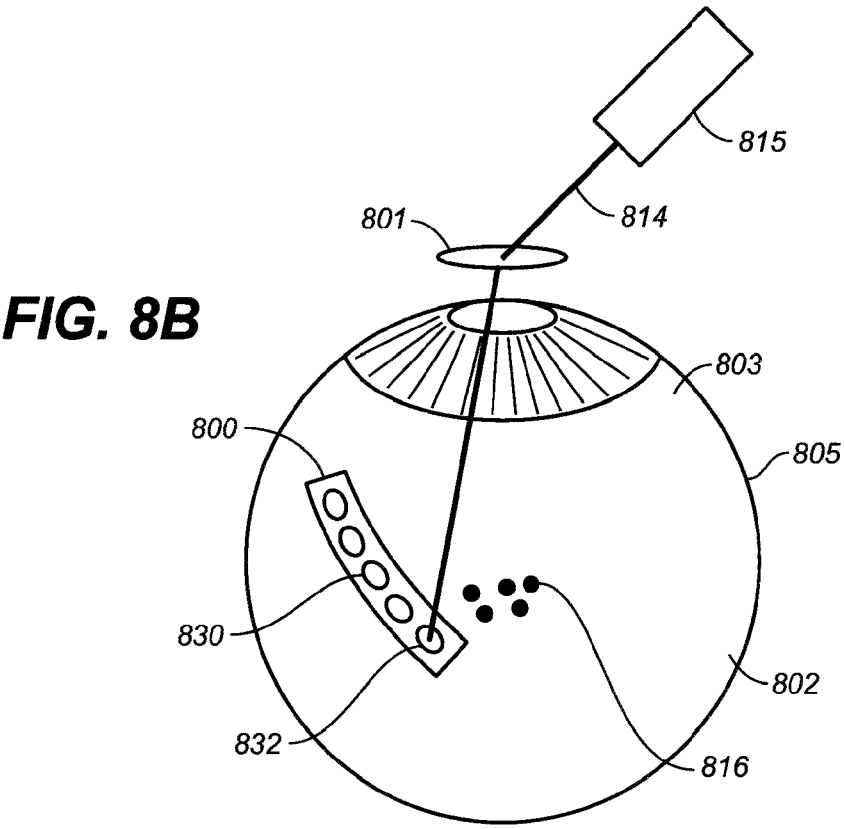

As described above, the drug delivery devices may be configured for implantation in a variety of body locations, including in an ocular region of a subject. In these variations, the devices may be configured for implantation into the vitreous cavity, the retina, the sclera, the cornea, and/or the conjunctiva of the subject. Referring now to FIGS. 8A to 8B, device 800 is configured to fit within the vitreous cavity 802 at the back of eye 805. An external first light source 810, e.g., a laser available to retinal specialists, may be used to irradiate a first reservoir 830 in device 800 to release a first agent 804 directly to the eye so that it can reach a desired target in the retinal region 803. The emission 812 of first light source 810 may not be significantly absorbed by any portion of device 800 except first reservoir 830, e.g., a first target region of first reservoir 830, thereby allowing selective release of only the first agent. In some cases, the emission 812 is not significantly absorbed by native tissues adjacent to device 800, thereby reducing the probability of damage to native tissues. As shown in FIG. 8B, a second reservoir 832 may be irradiated with a second light source 815 to release second agent 816 directly to the eye. Similar to first light source 810, second light source 815 may have an emission 814 that is not significantly absorbed by any portion of device 800 except second reservoir 832, e.g., a second target region of second reservoir 832, or by native tissues surrounding device 800. In some variations, the first and second light sources may be the same. In those cases, differentiation between reservoirs may be accomplished by differing the size and/or shape of the beam incident on the different reservoirs, and/or by using a light source that can be specifically directed at one reservoir without triggering another reservoir. In some variations, lens 801 may be used between light sources 810, 815 and the eye to filter the light and/or direct it onto the first or second target region. In other variations, the filtering/focusing lens 801 may be placed directly on the eye. The first and second agents may comprise sequential doses, which may be unit doses, of the same or a similar agent, e.g., to treat chronic conditions such as age-related macular degeneration. In those circumstances, implants may be left in the eye for years, with the spacing between doses being on the order of days, weeks, months, or longer.

Some drug delivery devices may comprise at least one reservoir that is configured to be loaded with an agent while the device is implanted in the subject. For example, for devices comprising first and second reservoirs, at least one of the first and second reservoirs may be configured to be loaded with its respective agent while the device is implanted in the subject. In other variations of these devices, at least one of the first and second reservoirs may be configured to be reloaded with a reload agent, which may be the same or different than either the first or the second agent. Some devices may be configured to accept replacement reservoirs (e.g., stand-alone reservoirs) that are pre-loaded with an agent after implantation. In these variations, replacement reservoirs may be reloaded through a self-sealing member in the device. One or more reloadable replacement reservoirs may comprise a target region configured for selectively-triggered drug release by a stimulus, e.g., a target region that allows selective absorption of certain wavelengths and/or energy or power densities of light to trigger release of the agent contained therein. In other variations, the loading and/or reloading of an agent into a device that has already been implanted in a subject may, for example, be achieved using a syringe. These devices may comprise an injection region, e.g., a septum that may self-seal after the syringe needle is removed. In other variations, an application (e.g., through a syringe) of a sealing material may be provided after the injection of an agent.

Figure 9A:
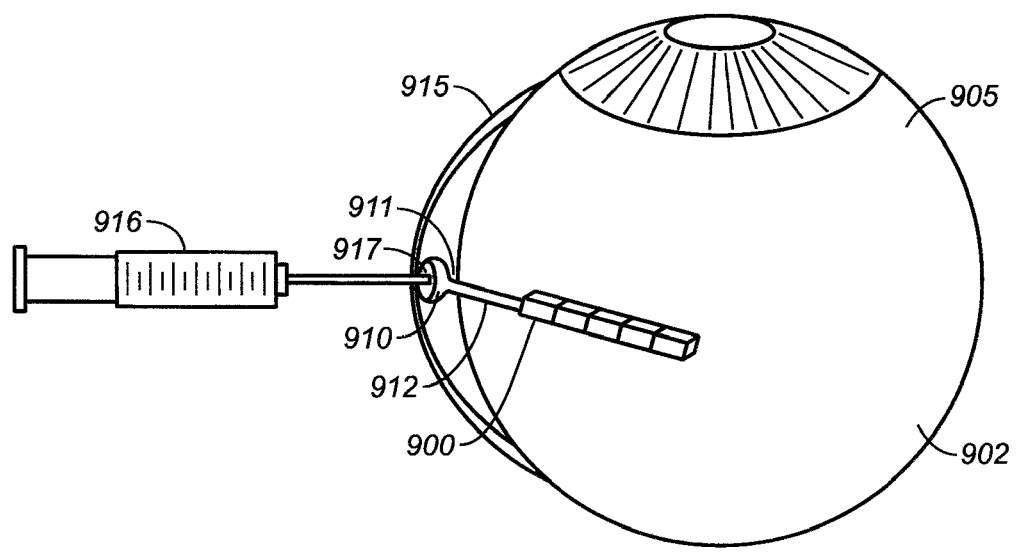
FIGS. 9A to 9D depict variations of drug delivery devices configured to be loaded with a drug after implantation into a subject.

In other variations of the devices described here, one or more reservoirs may be directly filled in an implanted device without the use of pre-loaded replacement reservoirs. Referring now to FIGS. 9A to 9D, device 900 has been implanted into the vitreous cavity 902 of eye 905. As shown in detail in FIG. 9B, device 900 comprises a filling port 910 that may extend outside the eye 905. A channel 912 interconnects a series of drug reservoirs 901 with the filling port 910. The drug reservoirs 901 may be separated from each other by a series of separation members 913, which may be, for example, one-way valves or self-sealing membranes. The filling port 910 may be external to the sclera, but remain within the conjunctiva or Tenon's capsule (indicated schematically by layer 915) to reduce the probability of infection via the entry point 911. As shown in FIG. 9A, filling port 910 may be configured to receive injection via a syringe 916. Filling port 910 may, for example, comprise a self-sealing injection region 917. In some variations of the methods, the syringe 916 may inject a drug into each of the reservoirs 901 in sequence, e.g., if they are separated by self-sealing membranes. In other variations of the methods, syringe 916 may fill only filling port 910, and the drug can then be pushed, e.g., by squeezing filling port 910, into the series of reservoirs 901 using one-way valves separating the reservoirs.

Figure 9B:
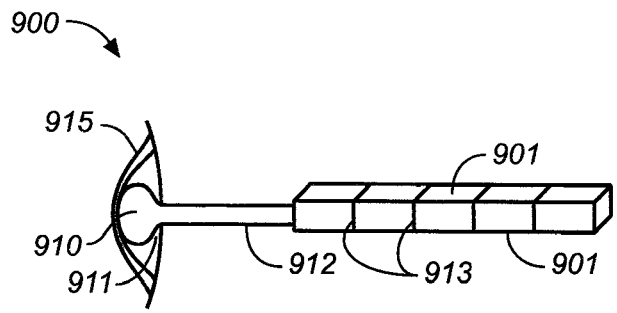
Figure 9C:
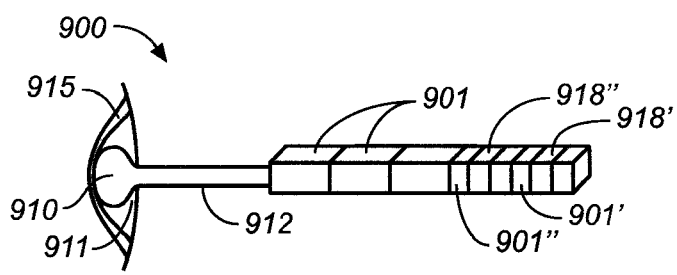

Referring now to FIG. 9C, the first reservoir 901' comprises a first target region 918' that may be configured to selectively respond to a first stimulus, e.g., absorb light from a first optical stimulus comprising light having a wavelength within a first frequency range. Thus, when the first reservoir receives a first stimulus (e.g., a first optical stimulus), the first reservoir may release a first agent contained therein. The second reservoir 901" does not release a second agent contained therein in response to the first stimulus. Instead, the second reservoir 901" may comprise a second target region 918" that is configured to selectively respond to a second stimulus (e.g., to absorb light from a second optical stimulus comprising light having a wavelength within a second wavelength range). Thus, in some variations, when light of an appropriate energy and/or power density having a wavelength within the second wavelength range is incident upon the second target region, the second reservoir may release the second agent. In other variations, the second reservoir may release the second agent in response to a second stimulus that is not necessarily optical, e.g., a thermal, electrical, mechanical, radiofrequency, chemical, ultrasound and/or magnetic stimulus.

Figure 9D:
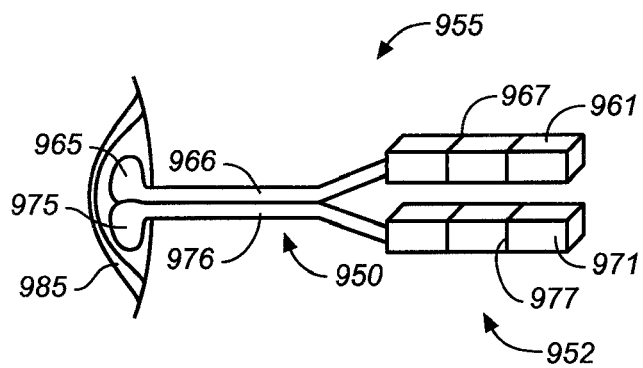

Some variations of devices that are configured to allow loading of one or more reservoirs after the drug delivery device has been implanted may include more than one externally accessible drug port. Referring now to FIG. 9D, device 950 has been implanted into the vitreous cavity 952 of eye 955. Device 950 comprises a first set of reservoirs 961 and a second set of reservoirs 971. The first set of reservoirs 961 are connected to a first externally accessible drug port 965 via channel 966. The first set of reservoirs may be separated from each other by first separation members 967, which may, for example, comprise self-sealing membranes or one-way valves. The second set of reservoirs 971 are connected to a second externally accessible drug port 975 via channel 976. The second drug port 975 may contain a different agent than the first drug port 965. The second set of reservoirs 971 may be separated from each other by second separation members 977, which may also comprise self-sealing membranes or one-way valves. The drug ports 975 and 965 may be external to the sclera, but remain within the conjunctiva or Tenon's capsule (indicated schematically by layer 985) and may, for example, each be charged with a syringe (not shown). In other variations, a first syringe (not shown) may extend down a length of channel 966 to fill reservoirs 961 that are separated by self-sealing membranes. Alternatively, or in addition, a second syringe (not shown) may extend down a length of channel 976 to fill reservoirs 971 that are separated by self-sealing membranes. In still other variations, the reservoirs 961 may be filled by squeezing filling port 965 to force a drug contained therein to reach the set of reservoirs 961 through one-way valves separating the reservoirs. Alternatively, or in addition, the reservoirs 971 may be filled by squeezing filling port 975 to force a drug contained therein to reach the set of reservoirs 971 via one-way valves separating the reservoirs.

The drug delivery devices described here may also be configured to be contained within implants that may be useful for repeat access. In such instances, the implants are configured to include one or more housings for receiving one or more of the drug delivery devices. The implants may have any suitable shape, dimension, geometry, etc., as further described below. The implants may also be configured to include one or more openings through which the drug delivery devices may be removed or replaced, or the reservoirs of the drug delivery devices triggered to release a drug contained therein, as also further described below. Repeat access of the implant may be useful when loading multiple drugs or reloading drugs into the reservoirs. Repeat access may also be beneficial during long term drug therapy. In this instance, not only may the reservoirs be reloaded with drug, but the drug delivery devices themselves may be replaced or switched as needed.

The implants may be placed within the body using a 20 gauge or smaller cannula. For example, a 21 gauge, a 22 gauge, a 23 gauge, a 25 gauge, or a 30 gauge or even smaller cannula may be used. The cannula may be part of an assembly, e.g., an injector that uses fluid or a viscoelastic substance to deploy the implant. In some instances, the injector may deploy the implant using a pusher, e.g., a wire or rod that is slidable within it. The cannula may also be used as an introducer to access a target area, tissue, space or potential space of the body. Here the implant may be deployed from the cannula using a pusher, e.g., a wire or rod that is slidable within it. In some variations, the cannula, injector, and/or pusher may be provided with markings to indicate how far they have been advanced. The drug delivery devices may be preloaded into the implant or loaded into the implant after placement at the target location.

When implants are to be placed within the eye, a 25 gauge cannula (needle) may be useful. The implants may be placed into an ocular region, e.g., the vitreous cavity, the retina, the sclera, the cornea, the conjunctiva, or a potential space within the orbit. When cannulas are employed, biocompatible sealants (e.g., fibrin, collagen, and thrombin based sealants and cyanoacrylate adhesives) may be used to help seal the opening in the ocular tissue. Suture closure of such openings may also be performed if needed. In some variations, the implants may be deployed so that a housing of the implant is flush or substantially flush with the external surface of the eye. If the drug delivery device was not preloaded into the implant, it may be placed into the implant by first accessing the housing with a cannula having a drug delivery device contained therein. The drug delivery device may then be placed into the housing by a cannula, an injector, or other cannula assembly. Some methods may involve incising the conjunctiva or other ocular tissue to place the implant at a target location. In such instances, the conjunctiva or other ocular tissue at or near the incision may be used to cover the access area of the housing, e.g., by pulling them over the access area and/or suturing flaps of tissue over the access area. Repeat access of the implant may be completed through any scar tissue formed at the site of incision.

The implant may be configured to have a proximal end, a distal end, a housing extended therebetween, and an access area at the proximal end for placement of the drug delivery device therethrough into the housing. The access area may be an opening of any cross-sectional geometry. For example, the opening may be cylindrical, ellipsoidal, triangular, quadrilateral, or irregular in cross-section. The cross-sectional geometry of the access area may or may not be adapted to match that or correspond with the cross-sectional geometry of the drug delivery device. The proximal end of the implant may also include a valve, e.g., a sealing valve, which prevents air from being introduced into the internal cavity. The distal end may or may not be closed.

One or more drug delivery devices may be included in the implant. The drug delivery devices may have one or more drug reservoirs that deliver one or multiple drugs. When multiple drug delivery devices are used with the implants, reservoirs of each device may deliver the same or different drugs. The same exemplary drugs and drug combinations described above may be delivered by the implants.

The implant may further include a fixation element to help attach it to body tissues. The fixation element may be located on any part of the implant and may have various configurations. For example, the fixation elements may be formed as barbs, hooks, spikes, tabs, and the like, and also roughened or texturized to aid implant attachment to tissues. In some instances, a suture is used alone or with a fixation element to attach the implant to tissue, e.g., the sclera.

Figure 11A:
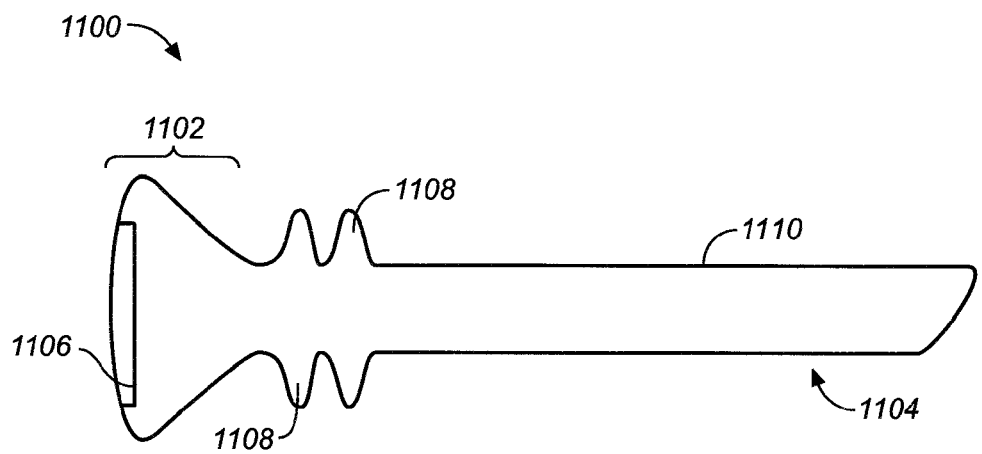
FIGS. 11A and 11B illustrate an exemplary implant comprising a fixation element.
Figure 11B:
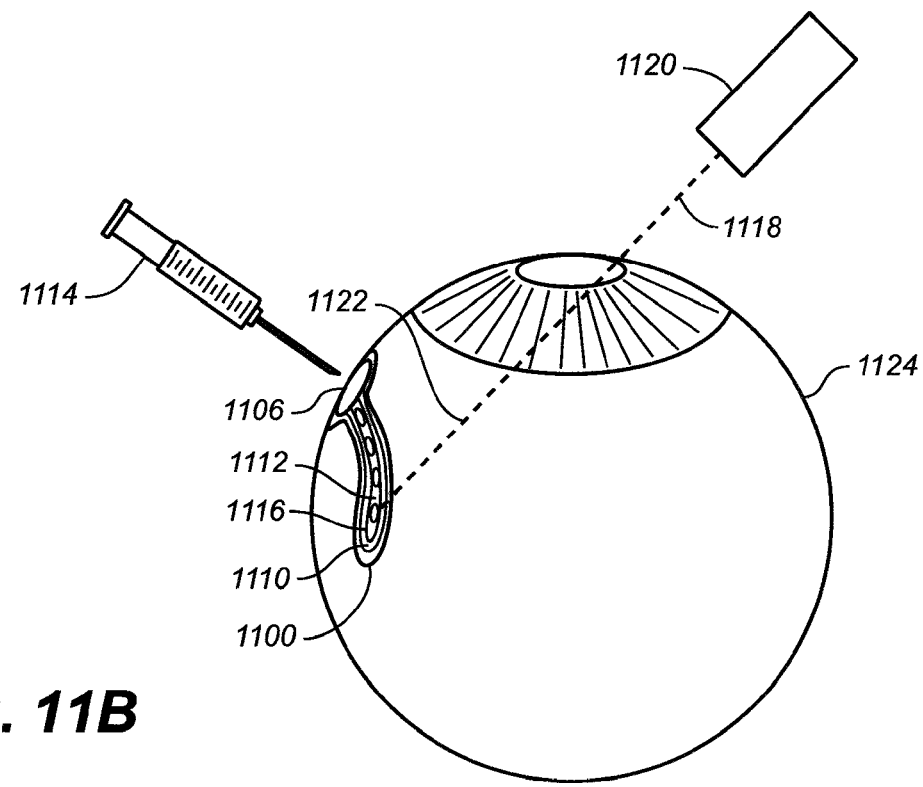

Referring to now to FIG. 11A, implant 1100 comprises a proximal end 1102, a distal end 1104, and an opening 1106 at the proximal end 1102. Tabs 1108 are provided as fixation elements near the proximal end 1102 to help attach the implant 1100 to body tissues. As shown in FIG. 11B, implant 1100 also includes a housing 1110 for holding the drug delivery device 1112 while it releases drug. The implant 1100 may be of varying dimensions and shape. In some variations, the implant 1100 may be from about 1.0 mm to about 1.0 cm in length. For example, the implant may be from about 3.5 mm to about 1.0 cm, about 0.5 cm to about 1.0 cm, or about 0.8 cm to about 1.0 cm in length. In certain variations, the implant is less than 1.0 mm in length. The dimensions of opening 1106 may also vary depending on such factors as the dimensions of the drug delivery device, number of drug delivery devices being included in the implant, tissue of implantation, etc., but will generally be configured to securely hold the drug delivery devices within the housing of the implant.

The implant housing may be made from the same or different materials used to form the drug delivery device. For example, the implant housing may be made from biocompatible materials such as silicone rubber and silicone elastomer, polymethylmethacrylate, polyolefins such as polypropylene and polyethylene, vinyl acetates, polyvinylchlorides, polyethylmethacrylates, polyurethanes, polyvinylpyrollidones, 2-pyrrolidones, polyacrylonitrile butadiene, polycarbonates, polyamides, fluoropolymers such as polytetrafluoroethylene (e.g., TEFLON™ polymer), polystyrenes, styrene acrylonitriles, cellulose acetate, acrylonitrile butadiene styrene, polymethylpentene, polysulfones, polyesters, polyimides, natural rubber, polyisobutylene rubber, polymethylstyrene, copolymers thereof, and blends thereof.

If biodegradable materials are to be used for the housing, non-limiting examples of suitable biodegradable polymers include alginate, cellulose and ester, collagen, dextran, elastin, fibrin, polysaccharides, hyaluronic acid, polyacetal, polyarylates (L-tyrosine-derived or free acid), poly(β-hydroxyesters), polyamides, poly(amino acid), polyalkanotes, polyalkylene alkylates, polyalkylene oxylates, polyalkylene succinates, polyanhydrides, polyanhydride esters, polyaspartimic acid, polylactic acid, polybutylene digloclate, poly (caprolactone), poly(caprolactone)/poly(ethylene glycol) copolymers, polycarbone, L-tyrosin-derived polycarbonates, polycyanoacrylates, polydihydropyrans, poly(dioxanone), poly-p-dioxanone, poly(ε-caprolactone-dimethyltrimethylene carbonate), poly(esteramide), polyesters, aliphatic polyesters, poly(etherester), polyethylene glycol/poly(orthoester) copolymers, poly(glutarunic acid), poly(glycolic acid), poly (glycolide), poly(glycolide)/poly(ethylene glycol) copolymers, poly(lactide), poly(lactide-co-caprolactone), poly(DL-lactide-co-glycolide), ply(lactide-co-glycolide)/poly (ethylene glycol) copolymers, poly(lactide)poly(ethylene glycol) copolymers, polypeptides, polyphosphazenes, polyphosphesters, polyphophoester urethanes, poly(propylene fumarate-co-ethylene glycol), poly(trimethylene carbone), polytyrosine carbonate, polyurethane, PorLastin or silk-elastin polymers, spider silk, tephaflex, terpolymer(copolymers of glycolide lactide or dimethyltrimethylene carbonate), and combinations, mixtures or copolymers thereof.

If transparency is desired, as further explained below, suitable transparent materials may be used. Materials with suitable transparency are typically polymers such as acrylic copolymers, acrylonitrile butadiene styrene (ABS), polycarbonate, polystyrene, polyvinyl chloride (PVC), polyethylene terephthalate glycol (PETG), and styrene acrylonitrile (SAN). Acrylic copolymers that may be useful include, but are not limited to, polymethyl methacrylate (PMMA) copolymer and styrene methyl methacrylate (SMMA) copolymer (e.g., Zylar 631® acrylic copolymer).

Figure 12A:
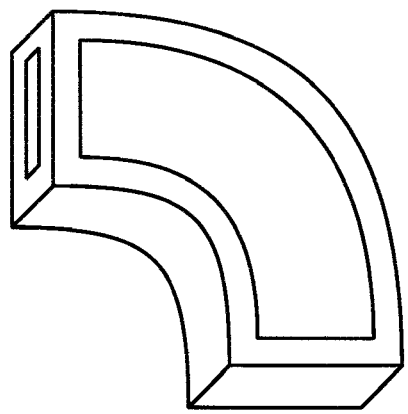
FIGS. 12A to 12D depict exemplary implant and housing configurations.
Figure 12B:
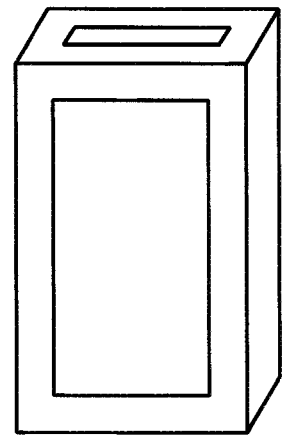
Figure 12C:
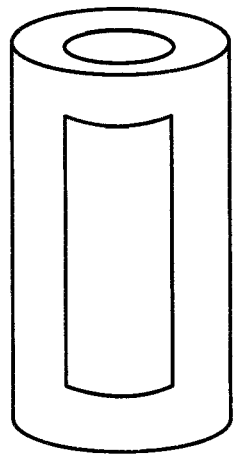
Figure 12D:
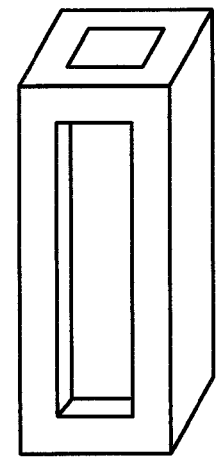

The implant may also be configured to have one or more openings (windows) in the implant wall so that reservoirs within the implant can be visualized, e.g., using an ophthalmoscope, slit lamp, ultrasound probe, optical coherence tomography (OCT), or other ocular imaging device (for direct or indirect visualization), and/or stimulation of the reservoirs through the opening may occur. The openings may be cut-outs of the implant wall or areas of the implant wall that are transparent. In some variations, the entire implant may be formed of a transparent material. For example, as shown in FIG. 11B, the drug delivery device 1112 that was introduced into implant 1100 in the eye 1124 through opening 1106 by a syringe 1114 can be visualized via window 1116 (using an ophthalmoscope). The emission 1118 from a light source 1120 may also be provided through window 1116 to trigger a reservoir in the drug delivery device 1112 to release a drug 1122. Although an optical stimulus is described here, any suitable type of stimulus may be used, including mechanical, chemical, electrical, magnetic, ultrasound, radiofrequency, thermal, and combinations thereof. A lens, such as lens 801 shown in FIGS. 8A and 8B, may be used here to focus and/or filter light onto the drug delivery device to trigger release of a drug. Further, although a substantially straight implant with a single housing is shown in FIGS. 11A and 11B, other configurations are contemplated. For example, the housing may be curved (FIG. 12A), rectangular (FIG. 12B), cylindrical (FIG. 12C), square (FIG. 12D), etc.

The implant may also include a single housing for holding the drug delivery device, or multiple housings, e.g., two (FIG. 13A), three (FIG. 13B, or four (FIG. 13C) or more housings. Of course, the implants may be provided with any number of housings. The number of windows provided may correspond to the number of housings present in the implant.

II. Kits

Kits are also described here. Some variations of kits comprise a drug delivery device configured for implantation, where the drug delivery device comprises at least one reservoir configured to be loaded with a drug, and at least one drug configured to be used with the drug delivery device. For example, some kits may comprise a drug or suite of drugs to be loaded directly into reservoirs of a drug delivery device. Other kits may include one or more reservoirs (e.g., stand-alone reservoirs) or replacement reservoirs configured to be loaded with one or more drugs. Such reservoirs or replacement reservoirs may be either pre-loaded or loaded by a clinician or other user. Thus, in some kits, the drug delivery device is configured to receive a replacement reservoir, either before or after implantation. Some variations of kits may comprise more than drug delivery device, e.g., a set of drug delivery devices. These kits may also include one or more drugs, e.g., drugs for direct loading into a reservoir and/or replacement reservoir. The kits may additionally include one or more implantation devices, e.g., multiple cannulas having varying sizes. Kits may optionally include one or more stimulus sources to be used to trigger release of an agent from a drug delivery device. Kits may, in some variations, include one or more tools for manipulating and/or securing devices, e.g., forceps, clamps, cutters, suturing tools, and the like. Kits may optionally include instructions for use.

Some variations of kits comprise a drug delivery device configured for implantation, and one or more implantation devices configured to implant the drug delivery device into a subject. In these kits, the drug delivery devices each comprise at least one reservoir configured to be loaded with an agent. The implantation device may, in some variations, comprise a 20 gauge, a 21 gauge, a 22 gauge, a 23 gauge, a 25 gauge or smaller cannula, e.g., a 30 gauge cannula, and in some variations, more than one implantation device may be provided in the kits, e.g., a set of cannulas having different sizes. These kits may also include one or more stimulus sources to be used to trigger release of an agent and/or one or more tools for manipulating and/or securing devices, e.g., forceps, clamps, cutters, suturing tools, or the like, and/or instructions for use.

The drug delivery devices used in any of the kits described here may be any drug delivery device described above. In kits comprising one or more drug delivery devices with multiple reservoirs that respond to different stimuli, more than one stimulus sources may be provided as part of the kits. Types of stimulus sources that may be included in any combination in kits include, in addition to optical sources, heating or cooling devices, electrical sources, chemicals (e.g., a solution having a certain pH or comprising a certain ion), radiofrequency sources, other radiative sources (e.g., ionizing radiation sources), mechanical sources (e.g., piezoelectric devices), ultrasound sources, magnets, or any combination thereof. Of course, more than one of any type of stimulus source may be provided, e.g., multiple optical sources which may be multiple lasers, e.g. two lasers may be included as part of a kit, where each laser is configured to trigger release of drugs from drug delivery devices that selectively absorb light having non-overlapping wavelength regions.

The kits may also comprise automated equipment to deliver one or more stimuli. For example, a stimulus may be coordinated with another event, such as a laser surgical procedure, or more than one stimulus may be coordinated or synchronized with another stimulus using a triggering device. Such automated triggering equipment may be preset, e.g., where the clinician or other user may be able to select from a variety of preset trigger sequences to initiate coordinated delivery of multiple drugs, or doses of drugs. In some cases, a clinician or other user may be able to provide input to vary an automated trigger sequence that has been adjusted for a particular subject or drug regimen.

As stated above, some kits may comprise one or more stimulus sources to trigger release of an agent from one or more implanted devices. In these variations of kits, a stimulus source may be preset or user-adjustable to deliver the appropriate stimulus to a particular region of a device, e.g., to a target region for a specific device reservoir. In general, the stimulus source may be preset or user-adjustable to trigger the release of the drug, while imparting little or no damage to surrounding tissues. For example, a drug delivery device in a kit may comprise a first reservoir housing a first drug, and a first target region configured to selectively absorb light over a first wavelength range. Those kits may include a first optical source capable of emitting light within the first wavelength range to the first target region. The first optical source may be preset, or user-adjustable, to deliver that wavelength of light with an appropriate spot-size, spot shape, pulse width, repetition rate, energy density and/or power density to trigger the release of the first drug from an implanted device without substantially damaging surrounding tissues.

In kits comprising one or more optical sources, the optical sources may be any suitable optical source. Optical sources may be light-emitting diodes, lamps, or lasers. Any of the optical sources, e.g., lamps, may have their emission filtered with one or more optical filters or other wavelength selection device to provide a desired wavelength range. Optical sources may be selected from lasers that are commonly available to retinal specialists or other ocular clinicians. An optical source may be selected from the group consisting of an argon ion laser, a Nd:YAG laser, e.g., a frequency-doubled Nd:YAG laser, a diode laser (e.g., a diode laser emitting red or green light), a Nd:YLF laser, a krypton ion laser, a pumped dye laser, a helium-neon laser, an excimer laser and a CuBr vapor laser. An optical source may emit continuous wave light, or pulsed light. Pulsed pumped dye lasers may be pumped by a frequency-doubled Nd:YAG or Nd:YLF laser, or an excimer laser. CW dye lasers may be pumped by an argon ion laser. Some kits may include at least one focusing apparatus and/or spatial filter to adjust an energy density or a power density of light emitted from an optical source. In some cases, one or more optical filters may be part of a kit to narrow a wavelength range light from an optical source. Thus, an optical source may comprise a pulsed or CW laser that emits coherent light at discrete wavelengths ranging from about 100 nm to about 10,000 nm. For example, the wavelengths may range from about 500 nm to about 1500 nm, from about 500 nm to about 700 nm, or from about 500 nm to about 600 nm. In some variations, the wavelengths may range from about 1040 nm to about 1064 nm.

Optical sources may be capable of providing any suitable energy or power density. As stated above, in general, the wavelength and/or energy or power density of an optical source may be selected to trigger the release of an agent from a reservoir in a drug delivery device without damaging or substantially damaging surrounding tissues. For example, sources providing energy densities of about 0.01 J/m$^2$ or less to about 5 J/m$^2$, and/or power densities of about 0.01 W/cm$^2$ or less to about 50 W/cm$^2$ may be used. If a pulsed light source is desired, a first optical source capable of pulse repetition rates of about 1.0 Hz to about 2000 kHz may be used. In some variations, the first optical source capable of pulse repetition rates of about 1.0 Hz to about 1.0 MHz may be used, e.g., about 1.0 Hz to about 20 Hz, or about 100 Hz to about 1.0 MHz, or about 500 Hz to about 1.0 MHz. The pulse duration of a pulsed optical source may be selected based on desired power densities. For example, pulse widths of about 1.0 ns to about 1.0 ms may be used, e.g., about 1.0 ns to about 100 ns, or about 100 ns to about 500 ns, or about 500 ns to about 1.0 μs, or about 1.0 μs to about 50 μs, or about 50 μs to about 500 μs, or about 500 μs to about 1.0 ms. In some variations, shorter pulse widths may used. For example, the pulse width may range from about 200 femtoseconds to about 3000 femtoseconds. An optical source may have any suitable spot size and shape, which may be further adjusted by one or more focusing lenses, mirrors, and/or spatial filters. For example, it may be desirable to adjust the spot shape and/or size of an optical source, e.g., using one or more lenses, focusing mirrors, and/or spatial filters to be approximately coincident with a target region to avoid unnecessary irradiation of surrounding areas and/or to utilize the spot size and/or shape as a selective trigger. Incident beams may have any suitable spot size and shape, and may have at least one dimension in the range of for example about 1 μm to about 200 μm, e.g., about 50 μm.

III. Methods

Methods are provided that incorporate the use of the drug delivery devices described above. The methods may, for example, be useful in treating a variety of conditions or indications, with non-limiting examples including age-related macular degeneration, diabetes-related conditions (e.g., diabetic retinopathy), cancer, glaucoma, retinal and choroidal disease, cataracts, dry eye syndrome, optic neuropathy, orbital disease, corneal conditions, and uveitis. The methods generally comprise implanting a drug delivery device into a subject. Any of the drug delivery devices, combinations of drug delivery devices, and/or kits described above may be used in the methods. These methods may involve applying various stimuli to the drug delivery devices to trigger a reservoir to release one or more agents to an anatomical region of the subject from the reservoir. Some methods may be directed to the treatment of ocular conditions, e.g., age-related macular degeneration. Other methods may be directed to conditions that are not necessarily limited to the ocular region of the subject, e.g., by administering an anti-tumor agent through the eye to reach a tumor elsewhere within the subject's body.

Some methods may involve the use of a stimulus to trigger release of a drug to a subject. In these methods, a drug delivery device may be implanted that comprises a first reservoir loaded with a first agent, and a first target region responsive to a first stimulus, e.g., a first optical stimulus, to trigger a reservoir to release the first agent. The methods may comprise stimulating the first target region with the first stimulus to trigger release of the first agent. For example, in some variations, the first target region may be configured to selectively absorb light over a first wavelength range, and the methods may include irradiating the first target region with light having a wavelength within the first wavelength range. Selective absorption of the light over the first wavelength range may, e.g., form a pore in a cap, wall, etc., of the reservoir, expose a semi-permeable or other rate-controlling membrane, or change other permeability properties of the reservoir or device material, as previously described. The first agent may then be released from the reservoir in any manner. For example, the first agent may be released actively (e.g., using pumps, injection, etc.) or passively (e.g., by diffusion or dissolution). The first agent may also be released according to any type of release profile. For example, the devices may be configured to release the first agent according to a continuous release, pulsed release, burst release (i.e., large initial release), bolus release (i.e., entire reservoir emptied immediately following being triggered by a stimulus), or zero-order release profiles. Other modified drug release profiles are also contemplated. For example, the reservoirs may be configured for controlled release (i.e., controlled rate of release over an extended time period) or sustained release (i.e., slow release over time, but not necessarily at a controlled rate of release) of the first agent. Of course, when multiple reservoirs are employed, any number and combination of stimuli may be used to trigger release of subsequent agents. Subsequent agents may also be released actively, passively, or by a combination of active and passive measures, and according to any release profile or combination of release profiles. Subsequent agents may also be released from different reservoirs in any order, simultaneously, or with any suitable intervening time interval.

Any suitable treatment regimen may be administered to the subject using the methods described here. For example, multiple agents may be released to provide a combination drug therapy, e.g., a concomitant combination drug therapy or a sequential drug therapy. In other methods, the multiple agents may be the same agent, and the methods of treatment may comprise delivering sequential doses of the same agent to the subject. For example, as illustrated in FIGS. 8A and 8B, the methods may comprise delivering a first stimulus and a second stimulus in sequence, where the first and/or second stimuli may be optical. Such methods may, for example, be used to deliver sequential doses to the subject. In other variations, multiple stimuli may be delivered in parallel, e.g., simultaneously or partially overlapping in time.

The methods may involve implanting the drug delivery device using any suitable technique, and into any suitable anatomical area of the subject. For example, the methods may include implanting the drug delivery devices into an ocular region of the subject, e.g., the vitreous cavity, the retina, the sclera, the cornea, or the conjunctiva. In some variations, the methods may comprise implanting the drug delivery device into the vitreous cavity of the subject through an implantation site under a conjunctiva and sealing the implantation site after implantation by pushing or closing the conjunctiva over the implantation site. Implantation may be done subconjunctivally or sub-Tenon's layer, or in any intraocular, periocular, or orbital location. In some cases, the drug delivery devices may be implanted using a surgical incision. In other cases, the drug delivery devices may be implanted through a 20 gauge or smaller cannula. For example, the drug delivery devices may be implanted through a 21 gauge, a 22 gauge, a 23 gauge, a 25 gauge, or a 30 gauge or even smaller cannula.

Some methods may involve loading an agent into a drug delivery device after the device has been implanted. In some cases, a reservoir may be reloaded after implantation, or a reservoir may be initially loaded after implantation. For example, these methods may include delivering a pre-loaded replacement reservoir into a drug delivery device. In these methods, the pre-loaded replacement reservoir may comprise a target region configured to selectively respond to a certain stimulus, e.g., to selectively absorb certain wavelengths of light to trigger release of the agent contained therein. Other methods may comprise implanting a sealable port that allows access to the drug delivery device after it has been implanted.

Certain methods for loading an agent into a drug delivery device after the device has been implanted into a subject may use devices similar to those illustrated in FIGS. 9A to 9D. Referring first to FIGS. 9A to 9C, the reservoirs 901 may be filled by extending a syringe into each of the series of reservoirs. These variations of methods may be used, for example, if the reservoirs are separated by self-sealing members. In other variations of methods, the reservoirs 901 may be filled by filling the filling port 910, e.g., with a syringe through a self-sealing injection region 917. Then the agent contained within filling port 910, e.g., as a solution, may be delivered into the series of reservoirs 901 by applying pressure, e.g., by squeezing, filling port 901 to force the agent into the successive reservoirs 901, e.g., through one-way valves interposed between the adjacent reservoirs. The methods may further involve sealing over the filling port using a conjunctiva or Tenon's capsule.

After a first reservoir 901' has been loaded with a first agent, methods may include stimulating a first target region 918' in first reservoir 901' with a first stimulus, e.g., a first optical stimulus, to trigger release of the first agent. The first target region may, for example, be configured to selectively absorb light over a first wavelength range. After a second reservoir 901" is filled with a second agent, the second agent may be released in response to a second stimulus, which may or may not be optical. In general, the first stimulus (e.g., the first optical stimulus) to first reservoir 901' may not interact with others of the reservoirs 901, so that the first agent is selectively released in response to the first stimulus. Some variations of the methods may comprise delivering a second stimulus (e.g., a second optical stimulus) to a second target region (e.g., target region 918") on a second reservoir (e.g., reservoir 901") to trigger release of a second agent. The second stimulus may, for example, comprise a second optical stimulus comprising light having a wavelength within a second wavelength range. In methods using first and second optical stimuli to initiate drug delivery from first and second reservoirs, respectively, the second wavelength range of the second optical stimulus may be selected to have little or no overlap with the first wavelength range of the first optical stimulus range that the first optical stimulus does not trigger release of the second agent, and the second optical stimulus does not trigger release of the first agent.

Other methods may comprise the use of more than one filling port to fill one or more reservoirs in a drug delivery device after the device has been implanted. Examples of such methods and associated drug delivery devices are shown in FIG. 9D. There, the methods may include charging the first and/or second sets of reservoirs with one or more syringes extending into the reservoirs. These methods may be used, for example, if adjacent reservoirs are separated by self-sealing membranes. Other methods may include charging the first filling port 965 with a first agent, and forcing the first agent to the first set of reservoirs 961, e.g., by applying pressure to the port 965. Alternatively, or in addition, the second filling port 975 may be filled with a second agent, and the second agent may be forced into the second set of reservoirs 971, e.g., by applying pressure to the port 975. These methods may be used, for example, if reservoirs 965 and/or 975 are separated and interconnected with one-way valves.

Any of the variations of methods described above may include retrieving, repositioning and/or visualizing devices. For example, methods may include retrieving and/or repositioning devices using one or more tethers, such as those illustrated in FIGS. 3A to 3C. Still other methods may comprise visualizing devices and/or portions of devices (e.g., separate reservoirs in devices). Such methods may use color-coded, shape-coded, and/or patterned devices and/or reservoirs (e.g., color-coded, shape-coded, and/or patterned target regions on reservoirs) to allow a clinician or other user to readily visualize a device and/or target region of a device. Of course, the methods may comprise the use of other tools to reposition and/or retrieve devices, such as forceps, clamps, hooks, and/or the like. Still other methods may comprise the use of other tools to visualize devices or portions of devices, such as fiberoptic scopes, or the like.

This disclosure is illustrative and not limiting. Further modifications will be apparent to one skilled in the art in light of this disclosure and such modifications are intended to fall within the scope of the appended claims. Each publication and patent application cited in the specification is incorporated herein by reference in its entirety as if each individual publication or patent application were specifically and individually put forth herein.

The invention claimed is:

1. A kit comprising:
   a drug delivery device for implantation into an eye, the device comprising:
   a device body comprising an elongated cylindrical structure in its implanted configuration having an annular wall defining a first reservoir configured to be loaded with a first agent; and
   a first target region of the annular wall extending circumferentially around the annular wall about the first reservoir, wherein the first target region is visually differentiated from other non-target portions of the annular wall without a target region;
   wherein the drug delivery device is configured to release the first agent from the first reservoir through an orifice created in the annular wall at the first target region by application of a first optical stimulus to the first target region, wherein the orifice may be formed at any position around a circumference of the annular wall in the first target region; and
   an implantation device configured to implant the drug delivery device into an eye of a patient.

2. The kit of claim 1, further comprising a first optical source configured to deliver the first optical stimulus to the first target region.

3. The kit of claim 2, wherein the first optical source is selected from the group consisting of: an argon ion laser, a Nd:YAG laser, a frequency-doubled Nd:YAG laser, a diode laser, a Nd:YLF laser, a helium-neon laser, a krypton ion laser, and a dye laser.

4. The kit of claim 2, wherein the first optical stimulus is a pulsed light.

5. The kit of claim 2, further comprising at least one focusing apparatus to adjust a power density of the first optical stimulus emitted from the first optical source.

6. The kit of claim 5, wherein the at least one focusing apparatus comprises a lens.

7. The kit of claim 1, wherein the implantation device comprises a 20 gauge or smaller cannula.

8. A drug delivery device for implantation into an eye, the drug delivery device comprising:
   a device body comprising an elongated cylindrical structure in its implanted configuration having an annular wall defining a first reservoir configured to be loaded with a first agent; and
   a first target region of the annular wall extending circumferentially around the annular wall about the first reservoir, wherein the first target region is visually differentiated from other non-target portions of the annular wall;
   wherein the drug delivery device is configured to release the first agent from the first reservoir through an orifice created in the annular wall at the first target region by application of a first optical stimulus to the first target region, wherein the orifice may be formed at any position around a circumference of the annular wall in the first target region.

9. The drug delivery device of claim 8, wherein the annular wall of the device body further defines: a second reservoir configured to be loaded with a second agent and further comprises a second target region extending circumferentially around the annular wall about the second reservoir.

10. The drug delivery device of claim 9, wherein the drug delivery device is configured to release the second agent from the second reservoir through an orifice created in the annular wall at the second target region by application of a second optical stimulus to the second target region.

11. The drug delivery device of claim 10, wherein the first optical stimulus has a first wavelength and the second optical stimulus has a second wavelength.

12. The drug delivery device of claim 10, wherein the first optical stimulus has a first power density and the second optical stimulus has a second power density.

13. The drug delivery device of claim 10, wherein the first optical stimulus has an incident beam having a first spot size and the second optical stimulus has an incident beam having a second spot size.

14. The drug delivery device of claim 10, wherein the first optical stimulus has an incident beam having a first spot geometry and the second optical stimulus has an incident beam having a second spot geometry.

15. The drug delivery device of claim 9, wherein the first reservoir is disposed in a first body section of the device body and the second reservoir is disposed in a second body section of the device body, the first body section and the second body section being coupled together.

16. The drug delivery device of claim 9, wherein the device body comprises a unitary body structure and a barrier is disposed between the first and second reservoirs.

17. The drug delivery device of claim 9, wherein the first agent and the second agent are the same agent.

18. The drug delivery device of claim 9, wherein the first agent and the second agent are different agents.

19. The drug delivery device of claim 9, wherein the annular wall of the device body further defines: a third reservoir configured to be loaded with a third agent and comprises a third target region extending circumferentially around the annular wall about the third reservoir,
   wherein the drug delivery device is configured to release the third agent from the third reservoir through an orifice created in the annular wall at the third target region in response to application of an optical stimulus to the third target region.

20. The drug delivery device of claim 9, wherein the first target region and the second target region of the annular wall is are visually differentiated from other non-target portions of the annular wall.

21. The drug delivery device of claim 20, wherein the first target region of the annular wall is visually differentiated from the second target region of the annular wall.

22. The drug delivery device of claim 9, wherein the first target region comprises a first chromophore that absorbs a first wavelength emitted from the first optical stimulus, and the second target region comprises a second chromophore that absorbs a second wavelength emitted from a second optical stimulus.

23. The drug delivery device of claim 9, wherein at least one of the first and second agents is selected from the group consisting of: anti-inflammatories, anti-infectives, anti-allergens, cholinergic agonists and antagonists, adrenergic agonists and antagonists, anti-glaucoma agents, agents for cataract prevention or treatment, neuroprotection agents, antioxidants, antihistamines, anti-platelet agents, anticoagulants, anti-thrombic agents, anti-scarring agents, antiproliferatives, anti-tumor agents, complement inhibitors, decongestants, vitamins, growth factors, anti-growth factor agents, gene therapy vectors, chemotherapy agents, protein kinase inhibitors, small interfering RNAs, limus family compounds, and combinations thereof.

24. The drug delivery device of claim 23, wherein at least one of the first and second agents comprises an anti-growth factor agent.

25. The drug delivery device of claim 24, wherein the anti-growth factor agent comprises an anti-VEGF agent.

26. The drug delivery device of claim 25, wherein the anti-VEGF agent comprises aflibercept.

27. The drug delivery device of claim 25, wherein the anti-VEGF agent comprises ranibizumab.

28. The drug delivery device of claim 25, wherein the anti-VEGF agent comprises bevacizumab.

29. The drug delivery device of claim 23, wherein at least one of the first and second agents comprises an anti-inflammatory agent.

30. The drug delivery device of claim 29, wherein the anti-inflammatory agent comprises a steroidal agent.

31. The drug delivery device of claim 30, wherein the steroidal agent comprises dexamethasone.

32. The drug delivery device of claim 30, wherein the steroidal agent comprises triamcinolone.

33. The drug delivery device of claim 30, wherein the steroidal agent comprises fluocinolone.

34. The drug delivery device of claim 23, wherein at least one of the first and second agents comprises a limus family compound.

35. The drug delivery device of claim 34, wherein the limus family compound comprises rapamycin.

36. The drug delivery device of claim 23, wherein at least one of the first and second agents comprises a complement inhibitor.

37. The drug delivery device of claim 9, wherein the first and second agents are selected to be part of a concomitant combination drug regimen.

38. The drug delivery device of claim 9, wherein the first and second agents are selected to be part of a sequential drug regimen.

39. The drug delivery device of claim 8, wherein the drug delivery device is configured to be free-floating in the eye.

40. The drug delivery device of claim 8, wherein the annular wall of the device body defines a plurality of reservoirs, each of the plurality of reservoirs configured to be loaded with a respective agent.

41. The drug delivery device of claim 40, wherein the plurality of reservoirs is at least five reservoirs.

42. The drug delivery device of claim 40, wherein the plurality of reservoirs is at least ten reservoirs.

43. The drug delivery device of claim 8, wherein the first optical stimulus comprises a first optical radiation having a first wavelength from about 500 nm to about 1500 nm.

44. The drug delivery device of claim 43, wherein the first wavelength is from about 500 nm to about 700 nm.

45. The drug delivery device of claim 44, wherein the first wavelength is from about 500 nm to about 600 nm.

46. The drug delivery device of claim 8, wherein the first optical stimulus is selected from the group consisting of an argon ion laser, a Nd:YAG laser, a frequency-doubled Nd:YAG laser, a diode laser, a Nd:YLF laser, a krypton laser, a dye laser, and a helium-neon laser.

47. The drug delivery device of claim 8, wherein the first target region of the annular wall comprises a chromophore capable of absorbing a first wavelength emitted from the first optical stimulus.

48. The drug delivery device of claim 8, wherein the first reservoir is configured to release the first agent through the orifice created in the annular wall at the first target region via diffusion into the eye.

49. The drug delivery device of claim 8, wherein the first reservoir is configured to release the first agent in a sustained manner after the formation of the first orifice in the annular wall at the first target region.

50. The drug delivery device of claim 8, wherein the device is configured for the treatment of age-related macular degeneration.

51. The drug delivery device of claim 8, wherein the device is configured to be implanted in a vitreous cavity, a retina, a sclera, a cornea, or a conjunctiva of the eye of a patient.

52. The drug delivery device of claim 8, wherein the device is configured for the treatment of diabetic retinopathy.

53. The drug delivery device of claim 8, wherein the device is configured for treatment of macular degeneration.

54. The drug delivery device of claim 8, wherein the device is configured for treatment of glaucoma.

55. The drug delivery device of claim 8, wherein the first target region of the annular wall extends about 360 degrees circumferentially around the annular wall about the first reservoir.

* * * * *